United States Patent
Bauer et al.

(10) Patent No.: US 6,806,272 B2
(45) Date of Patent: Oct. 19, 2004

(54) DIHYDROPTERIDINONES, PROCESSES FOR PREPARING THEM AND THEIR USE AS PHARMACEUTICAL COMPOSITIONS

(75) Inventors: Eckhart Bauer, Biberach (DE); Steffen Breitfelder, Assmannshardt (DE); Christian Eickmeier, Mittelbiberach (DE); Matthias Grauert, Biberach (DE); Matthias Hoffmann, Mittelbiberach (DE); Thorsten Lehmann-Lintz, Ochsenhausen (DE); Gerald Pohl, Biberach (DE); Jens Quant, Guntramsdorf (AT); Norbert Redemann, Biberach (DE); Gisela Schnapp, Biberach-Rindenmoos (DE); Martin Steegmaier, Wien (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 89 days.

(21) Appl. No.: 10/226,710

(22) Filed: Aug. 23, 2002

(65) Prior Publication Data

US 2004/0029885 A1 Feb. 12, 2004

Related U.S. Application Data

(60) Provisional application No. 60/332,681, filed on Nov. 14, 2001.

(30) Foreign Application Priority Data

Sep. 4, 2001 (DE) .......................... 101 43 272

(51) Int. Cl.$^7$ .................. C07D 487/04; A61K 31/4985
(52) U.S. Cl. ...................... 514/250; 544/257
(58) Field of Search ........................... 544/257; 514/250

(56) References Cited

U.S. PATENT DOCUMENTS 5,698,556 A  12/1997  Chan ........................ 514/429

FOREIGN PATENT DOCUMENTS

| EP | 0 399 856 A1 | 11/1990 |
| EP | 0 429 149 A1 | 5/1991 |
| WO | WO 01/19825 A1 | 3/2001 |
| WO | WO 02/076954 A1 | 10/2002 |

OTHER PUBLICATIONS

The Merck Manual of Medical Information– Home Edition, Section 17, Infections, Chapter 184 on the web site http://www.merck.com/mrkshared/mmanual_home/sec17/184.jsp, downloaded on Nov. 26, 2003.*

* cited by examiner

Primary Examiner—Richard L. Raymond
Assistant Examiner—Kahsay Habte
(74) Attorney, Agent, or Firm—Robert P. Raymond; Anthony P. Bottino; Timothy X. Witkowski

(57) ABSTRACT

The present invention relates to new dihydropteridinones of the formula (I)

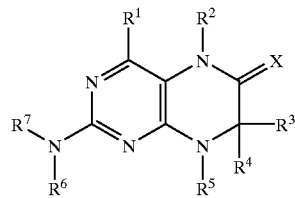

wherein the groups X, $R^1$, $R^2$, $R^3$, $R^4$, $R^5$ and $R^7$ have the meanings given in the claims and the specification, the isomers thereof, processes and intermediates for preparing these dihydropteridinones as well as the use thereof as pharmaceutical compositions.

10 Claims, No Drawings

DIHYDROPTERIDINONES, PROCESSES FOR PREPARING THEM AND THEIR USE AS PHARMACEUTICAL COMPOSITIONS

APPLICATION DATA

This application claims benefit to DE 101 43 272.0 filed Sep. 4, 2001 and U.S. provisional application No. 60/332681 filed Nov. 14, 2001.

FIELD OF THE INVENTION

The present invention relates to new dihydropteridinones of general formula (I)

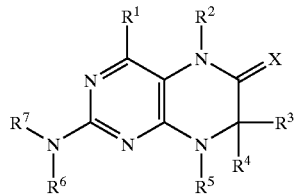

wherein the groups X, $R^1$, $R^2$, $R^3$, $R^4$, $R^5$, $R^6$ and $R^7$ have the meanings given in the claims and specification, the isomers thereof, processes for preparing these dihydropteridinones and the use thereof as pharmaceutical compositions.

BACKGROUND OF THE INVENTION

Pteridinone derivatives are known from the prior art as active substances with an antiproliferative activity. WO 01/019825 describes the use of pteridinone derivatives for the treatment of neoplastic and viral diseases. The resistance of many types of tumours calls for the development of new pharmaceutical compositions for combating tumours.

The aim of the present invention is to prepare new compounds with an antiinflammatory and antiproliferative activity.

DETAILED DESCRIPTION OF THE INVENTION

Surprisingly it has been found that compounds of general formula (I) wherein the groups X and $R^1$ to $R^7$ have the meanings given hereinafter act as inhibitors of specific cell cycle kinases. Thus, the compounds according to the invention may be used for example to treat diseases connected with the activity of specific cell cycle kinases and characterised by excessive or abnormal cell proliferation.

The present invention therefore relates to compounds of general formula (I)

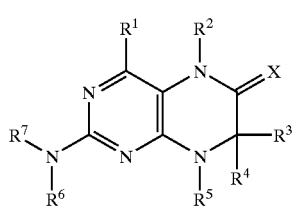

(I)

wherein $R^1$ denotes a group selected from among hydrogen, $NH_2$, XH, halogen and a $C_1$–$C_3$-alkyl group optionally substituted by one or more halogen atoms, $R^2$ denotes a group selected from among hydrogen, CHO, XH, —X—$C_1$–$C_2$-alkyl and an optionally substituted $C_1$–$C_3$-alkyl group, $R^3$, $R^4$ which may be identical or different denote a group selected from among optionally substituted $C_1$–$C_{10}$-alkyl, $C_2$–$C_{10}$-alkenyl, $C_2$–$C_{10}$-alkynyl, aryl, heteroaryl, $C_3$–$C_8$-cycloalkyl, $C_3$–$C_8$-heterocycloalkyl, —X-aryl, —X-heteroaryl, —X-cycloalkyl, —X-heterocycloalkyl, —$NR^8$-aryl, —$NR^8$-heteroaryl, —$NR^8$-cycloalkyl and —$NR^8$-heterocycloalkyl, or a group selected from among hydrogen, halogen, $COXR^8$, $CON(R^8)_2$, $COR^8$ and $XR^8$, or $R^3$ and $R^4$ together denote a 2- to 5-membered alkyl bridge which may contain 1 to 2 heteroatoms, $R^5$ denotes hydrogen or a group selected from among optionally substituted $C_1$–$C_{10}$-alkyl, $C_2$–$C_{10}$-alkenyl, $C_2$–$C_{10}$-alkynyl, aryl, heteroaryl and —$C_3$–$C_6$-cycloalkyl, or $R^3$ and $R^5$ or $R^4$ and $R^5$ together denote a saturated or unsaturated $C_3$–$C_4$-alkyl bridge which may contain 1 to 2 heteroatoms, $R^6$ denotes optionally substituted aryl or heteroaryl, $R^7$ denotes hydrogen or —CO—X—$C_1$–$C_4$-alkyl, and X in each case independently of one another denotes O or S, $R^8$ in each case independently of one another denotes hydrogen or a group selected from among optionally substituted $C_1$–$C_4$-alkyl, $C_2$–$C_4$-alkenyl, $C_2$–$C_4$-alkynyl and phenyl, optionally in the form of the tautomers, the racemates, the enantiomers, the diastereomers and the mixtures thereof, and optionally the pharmacologically acceptable acid addition salts thereof.

Preferred compounds of formula (I) are those wherein

X and $R^6$ have the meaning indicated, and $R^1$ denotes hydrogen, $R^2$ denotes a group selected from among a CHO, OH, and $CH_3$ group, $R^3$, $R^4$ which may be identical or different denote a group selected from among hydrogen, optionally substituted $C_1$–$C_6$-alkyl, $C_2$–$C_6$-alkenyl, $C_2$–$C_6$-alkynyl, $C_3$–$C_7$-cycloalkyl, or $R^3$ and $R^4$ together denote a $C_2$–$C_5$-alkyl bridge, $R^5$ denotes a group selected from among optionally substituted $C_1$–$C_{10}$-alkyl, $C_2$–$C_{10}$-alkenyl, $C_2$–$C_{10}$-alkynyl, $C_3$–$C_6$-cycloalkyl and $C_3$–$C_6$-cycloalkenyl, or $R^3$ and $R^5$ or $R^4$ and $R^5$ together denote a saturated or unsaturated $C_3$–$C_4$-alkyl bridge which may contain 1 to 2 heteroatoms, and $R^7$ denotes hydrogen, optionally in the form of the tautomers, the racemates, the enantiomers, the diastereomers and the mixtures thereof, and optionally the pharmacologically acceptable acid addition salts thereof.

Particularly preferred compounds of formula (I) are those wherein $R^1$–$R^5$, $R^7$, $R^8$ and X have the meaning indicated, and $R^6$ denotes a group of general formula

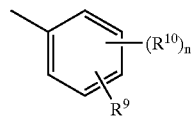

wherein n denotes 1, 2, 3 or 4, $R^9$ denotes a group selected from among optionally substituted $C_1$–$C_6$-alkyl, $C_2$–$C_6$-alkenyl, $C_2$–$C_6$-alkynyl, —CONH—$C_1$–$C_{10}$-alkylene, —O-aryl, —O-heteroaryl, —O-cycloalkyl, —O-heterocycloalkyl, aryl, heteroaryl, cycloalkyl and heterocycloalkyl or a group selected from among —O—$C_1$–$C_6$-alkyl-$Q^1$, —CONR$^8$—$C_1$–$C_{10}$-alkyl-$Q^1$, —CONR$^8$—$C_2$–$C_{10}$-alkenyl-$Q^1$, —CONR$^8$—$Q^2$, halogen, OH, —SO$_2$R$^8$, —SO$_2$N(R$^8$)$_2$, —COR$^8$, —COOR$^8$, —N(R$^8$)$_2$, —NHCOR$^8$, CONR$^8$OC$_1$–$C_{10}$ alkylQ$^1$ and CONR$^8$OQ$^2$, $Q^1$ denotes hydrogen, —NHCOR$^8$, or a group selected from among an optionally substituted —NH-aryl, —NH-heteroaryl, aryl, heteroaryl, $C_3$–$C_8$-cycloalkyl- and heterocycloalkyl group, $Q^2$ denotes hydrogen or a group selected from among an optionally substituted aryl, heteroaryl, $C_3$–$C_8$-heterocycloalkyl, $C_3$–$C_8$-cycloalkyl- and $C_1$–$C_4$-alkyl-$C_3$–$C_8$-cycloalkyl group, $R^{10}$ which may be identical or different denotes a group selected from among optionally substituted $C_1$–$C_6$-alkyl, $C_2$–$C_6$-alkenyl and $C_2$–$C_6$-alkynyl, —O—$C_1$–$C_6$-alkyl, —O—$C_2$–$C_6$-alkenyl, —O—$C_2$–$C_6$-alkynyl, $C_3$–$C_6$-heterocycloalkyl and $C_3$–$C_6$-cycloalkyl, or a group selected from among hydrogen, —CONH$_2$, —COOR$^8$, —OCON(R$^8$)$_2$, —N(R$^8$)$_2$, —NHCOR$^8$, —NHCON(R$^8$)$_2$, —NO$_2$ and halogen, or adjacent groups $R^9$ and $R^{10}$ together denote a bridge of general formula

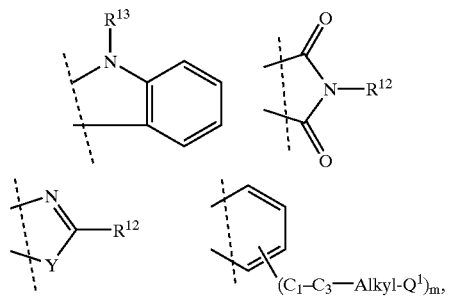

Y denotes O, S or NR$^{11}$, m denotes 0, 1 or 2

$R^{11}$ denotes hydrogen or $C_1$–$C_2$-alkyl, and $R^{12}$ denotes hydrogen or a group selected from among optionally substituted phenyl, pyridyl, pyrazinyl, pyrimidinyl, pyridazinyl, —$C_1$–$C_3$-alkyl-phenyl, —$C_1$–$C_3$-alkyl-pyridyl, —$C_1$–$C_3$-alkyl-pyrazinyl, —$C_1$–$C_3$-alkyl-pyrimidinyl and —$C_1$–$C_3$-alkyl-pyridazinyl, $R^{13}$ denotes $C_1$–$C_6$-alkyl, optionally in the form of the tautomers, the racemates, the enantiomers, the diastereomers and the mixtures thereof, and optionally the pharmacologically acceptable acid addition salts thereof.

Particularly preferred are compounds of formula (I) wherein $R^3$–$R^6$, $R^8$ and X have the meaning indicated, and $R^1$ denotes hydrogen, $R^2$ denotes CH$_3$, and $R^7$ denotes hydrogen, optionally in the form of the tautomers, the racemates, the enantiomers, the diastereomers and the mixtures thereof, and optionally the pharmacologically acceptable acid addition salts thereof.

The invention further relates to compounds of formula (I), wherein X and $R^1$–$R^7$ have the meanings indicated, for use as pharmaceutical compositions.

Of particular importance according to the invention are compounds of formula (I), wherein X and $R^1$–$R^7$ have the meaning indicated, for use as pharmaceutical compositions with an antiproliferative activity.

The invention also relates to the use of a compound of formula (I), wherein X and $R^1$–$R^7$ have the meaning indicated, for preparing a pharmaceutical composition for the treatment and/or prevention of cancer, infections, inflammatory and autoimmune diseases.

The invention also relates to a method of treating and/or preventing cancer, infections, inflammatory and autoimmune diseases, characterised in that a patient is given an effective amount of a compound of formula (I), wherein X and $R^1$–$R^7$ have the meanings indicated.

The invention also relates to pharmaceutical preparations, containing as active substance one or more compounds of general formula (I), wherein X and $R^1$–$R^7$ have the meanings indicated, or the physiologically acceptable salts thereof, optionally combined with conventional excipients and/or carriers.

The invention also relates to a process for preparing a compound of general formula (I),

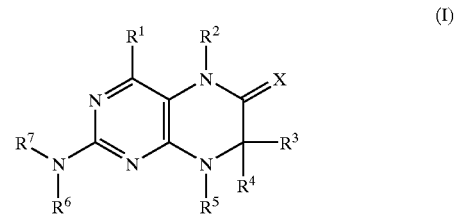

(I)

wherein $R^1$–$R^7$ and X are as hereinbefore defined, characterised in that a compound of general formula (II)

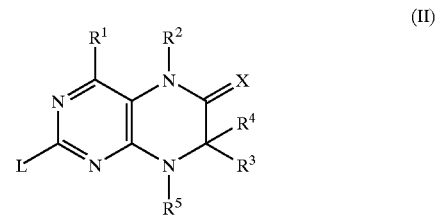

(II)

wherein $R^1$–$R^5$ and X are as hereinbefore defined and L is a leaving group, is reacted with an optionally substituted compound of general formula (III)

(III)

wherein $R^6$ and $R^7$ are as hereinbefore defined.

The invention also relates to a compound of formula (II),

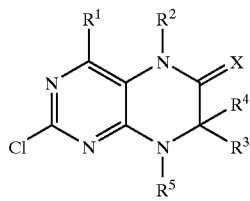
(II)

wherein $R^1$–$R^5$ and X are as hereinbefore defined. Compounds of formula (II) are important intermediate products for preparing the compounds of formula (I) according to the invention.

The invention also relates to a process for preparing a compound of general formula (I),

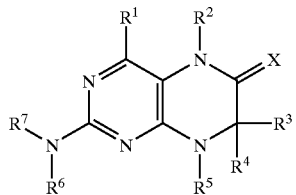
(I)

wherein $R^6$ denotes a group of general formula,

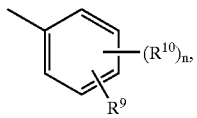

$R^9$ denotes an optionally substituted group —CONH—$C_1$–$C_{10}$-alkylene or a group selected from among —CONR$^8$—$C_1$–$C_{10}$-alkyl-$Q^1$, —CONR$^8$—$C_2$–$C_{10}$-alkenyl-$Q^1$, —CONR$^8$—$Q^2$ and —COOR$^8$, and $R^1$–$R^5$, $R^7$, $R^{10}{}_1$, n and X are as hereinbefore defined, characterised in that a compound of general formula (IA)

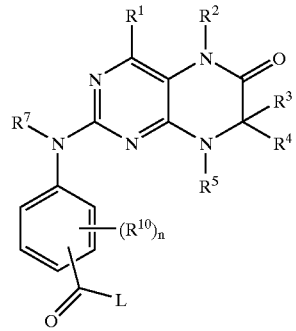
(IA)

wherein $R^1$ to $R^5$, $R^7$ and $R^{10}$ are as hereinbefore defined, and

L denotes a leaving group, is reacted with a primary or secondary amine to form the corresponding amide or is reacted with an alcohol to form the corresponding ester.

The term alkyl groups, including alkyl groups which are a part of other groups, denotes branched and unbranched alkyl groups with 1 to 10 carbon atoms, preferably 1–6, most preferably 1–4 carbon atoms, such as, for example: methyl, ethyl, propyl, butyl, pentyl, hexyl, heptyl, octyl, nonyl and decyl. Unless otherwise stated, the abovementioned terms propyl, butyl, pentyl, hexyl, heptyl, octyl, nonyl and decyl include all the possible isomeric forms. For example, the term propyl includes the two isomeric groups n-propyl and iso-propyl, the term butyl includes n-butyl, iso-butyl, sec. butyl and tert.-butyl, the term pentyl includes iso-pentyl, neopentyl, etc.

In the abovementioned alkyl groups one or more hydrogen atoms may optionally be replaced by other groups. For example these alkyl groups may be substituted by the halogen atoms fluorine, chlorine, bromine or iodine. The substituents fluorine and chlorine are preferred. The substituent chlorine is particularly preferred. All the hydrogen atoms of the alkyl group may optionally also be replaced.

Similarly, in the abovementioned alkyl groups, unless otherwise stated, one or more hydrogen atoms may optionally be replaced for example by an optionally substituted group selected from among CN, OCOCH$_3$, aryl, preferably phenyl, heteroaryl, preferably thienyl, thiazolyl, imidazolyl, pyridyl, pyrimidyl or pyrazinyl, saturated or unsaturated heterocycloalkyl, preferably pyrazolyl, pyrrolidinyl, piperidinyl, piperazinyl or tetrahydro-oxazinyl, an amine group, preferably methylamine, benzylamine, phenylamine or heteroarylamine, saturated or unsaturated bicyclic ring systems, preferably benzimidazolyl and cycloalkyl, preferably cyclohexyl or cyclopropyl.

The term alkyl bridge, unless otherwise stated, denotes branched and unbranched alkyl groups with 2 to 5 carbon atoms, for example propylene, isopropylene, n-butylene, iso-butyl, sec. butyl and tert.-butyl etc. bridges. Propylene and butylene bridges are particularly preferred. In the alkyl bridges mentioned 1 to 2 C-atoms may optionally be replaced by one or more heteroatoms selected from among oxygen, nitrogen or sulphur.

The term alkenyl groups (including those which are a part of other groups) denotes branched and unbranched alkylene groups with 2 to 10 carbon atoms, preferably 2–6 carbon atoms, most preferably 2–3 carbon atoms, provided that they have at least one double bond. Examples include: ethenyl, propenyl, butenyl, pentenyl etc. Unless otherwise stated, the abovementioned terms propenyl, butenyl, etc also include all the possible isomeric forms. For example, the term butylene includes n-butenyl, 1-methylpropenyl, 2-methylpropenyl, 1,1-dimethylethenyl, 1,2-dimethylethenyl etc.

In the abovementioned alkenyl groups, unless otherwise stated, one or more hydrogen atoms may optionally be replaced by other groups. For example, these alkyl groups may be substituted by the halogen atoms fluorine, chlorine, bromine or iodine. The substituents fluorine and chlorine are preferred. The substituent chlorine is particularly preferred. All the hydrogen atoms of the alkenyl group may optionally also be replaced.

The term alkynyl groups (including those which are a part of other groups) denotes branched and unbranched alkynyl groups with 2 to 10 carbon atoms, provided that they have at least one triple bond, for example ethynyl, propargyl, butynyl, pentynyl, hexynyl etc., preferably ethynyl or propynyl.

In the abovementioned alkynyl groups, unless otherwise stated, one or more hydrogen atoms may optionally be replaced by other groups. For example, these alkyl groups may be substituted by the halogen atoms fluorine, chlorine, bromine or iodine. The substituents fluorine and chlorine are preferred. The substituent chlorine is particularly preferred. All the hydrogen atoms of the alkynyl group may optionally also be replaced.

The term aryl denotes an aromatic ring system with 6 to 14 carbon atoms, preferably 6 or 10 carbon atoms, preferably phenyl, which, unless otherwise stated, may carry one or more of the following substituents, for example: OH, $NO_2$, CN, —$OCHF_2$, —$OCF_3$, —$NH_2$, halogen, for example fluorine, chlorine, bromine or iodine, preferably fluorine or chlorine, $C_1$–$C_{10}$-alkyl, preferably $C_1$–$C_5$-alkyl, preferably $C_1$–$C_3$-alkyl, most preferably methyl or ethyl, —O—$C_1$–$C_3$-alkyl, preferably —O-methyl or —O-ethyl, —N-methyl-tetrahydro-oxazinyl, —COOH, —COO—$C_1$–$C_4$-alkyl, preferably —$COOCH_2CH_3$, —COO—$C(CH_3)_3$ or —$COOCH_3$, —$CONH_2$, —CONH—$C_1$–$C_{10}$-alkyl, while this alkyl may optionally be further substituted, optionally substituted —CONH—$C_3$–$C_6$-cycloalkyl, preferably optionally substituted —CONH-cyclopentyl, optionally substituted —CONH-heterocycloalkyl, preferably piperidinyl, pyrrolidinyl or piperazinyl, optionally substituted —CONH-heteroaryl, preferably optionally substituted —CONH-pyridyl, optionally substituted —CONH-aryl, preferably optionally substituted —CONH-phenyl, —CONMe$C_1$–$C_3$-alkyl, while this alkyl may optionally be further substituted, preferably —$CONMeCH_2$-pyridyl, benzimidazole or a group of formula

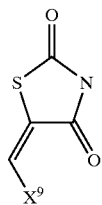

Examples of 5–10-membered mono- or bicyclic heteroaryl rings wherein up to three C-atoms may be replaced by one or more heteroatoms selected from among oxygen, nitrogen or sulphur include furan, thiophene, pyrrole, pyrazole, imidazole, triazole, tetrazole, pyridine, pyridazine, pyrimidine, pyrazine, triazine, oxazole, isoxazole, thiazole, thiadiazole and oxadiazole, while each of the abovementioned heterocycles may optionally also be annellated onto a benzene ring, preferably benzimidazole, and unless otherwise stated these heterocycles may for example carry one or more of the following substituents: OH, $NO_2$, CN, —$OCHF_2$, —$OCF_3$, —$NH_2$, halogen, preferably fluorine or chlorine, $C_1$–$C_{10}$-alkyl, preferably $C_1$–$C_5$-alkyl, preferably $C_1$–$C_3$-alkyl, most preferably methyl or ethyl, —O—$C_{1-C3}$-alkyl, preferably —O-methyl or —O-ethyl, -methyl-N-tetrahydro-oxazinyl, —COOH, —COO—$C_1$–$C_4$-alkyl, preferably —COO—$C(CH_3)_3$ or —$COOCH_3$, —$CONH_2$, optionally substituted phenyl, optionally substituted heteroaryl, preferably optionally substituted pyridyl or pyrazinyl, —CONH—$C_1$–$C_{10}$-alkyl, while this alkyl may itself optionally be substituted, optionally substituted —CONH—$C_3$–$C_6$-cycloalkyl, preferably optionally substituted —CONH-cyclopentyl, optionally substituted —CONH-heteroaryl, preferably optionally substituted —CONH-pyridyl, optionally substituted —CONH-aryl, preferably optionally substituted —CONH-phenyl, —CONMe$C_1$–$C_3$-alkyl, while this alkyl may itself optionally be substituted, preferably —$CONMeCH_2$-pyridyl, benzimidazole or a group of formula

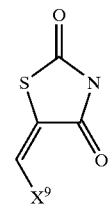

The term cycloalkyl groups denotes, for example, saturated or unsaturated cycloalkyl groups with 3–8 carbon atoms, for example cyclopropyl, cyclobutyl, cyclopentyl, cyclopentenyl, cyclohexyl, cyclohexenyl, cycloheptyl or cyclooctyl, preferably cyclopropyl, cyclopentyl or cyclohexyl, while each of the abovementioned cycloalkyl groups may optionally also carry one or more substituents, preferably=O, or may be annellated to a benzene ring.

"=O" denotes an oxygen atom linked via a double bond.

The term heterocycloalkyl groups, unless otherwise described in the definitions, may denote 5-, 6- or 7-membered, saturated or unsaturated heterocycles, which may contain nitrogen, oxygen or sulphur as heteroatoms, for example tetrahydrofuran, tetrahydrofuranon, γ-butyrolactone, α-pyran, γ-pyran, dioxolane, tetrahydropyran, dioxane, dihydrothiophene, thiolan, dithiolan, pyrroline, pyrrolidine, pyrazoline, pyrazolidine, imidazoline, imidazolidine, tetrazole, piperidine, pyridazine, pyrimidine, pyrazine, piperazine, triazine, tetrazine, morpholine, thiomorpholine, diazepan, oxazine, tetrahydro-oxazinyl, isothiazole and pyrazolidine, preferably pyrazolyl, pyrrolidinyl, piperidinyl, piperazinyl or tetrahydro-oxazinyl, while the heterocycle may optionally be substituted.

Generally, the term halogen denotes fluorine, chlorine, bromine or iodine.

The leaving group L denotes either identical or different leaving groups such as for example chlorine, bromine, iodine, methanesulphonyl, trifluoromethanesulphonyl or p-toluenesulphonyl, preferably chlorine.

The compounds according to the invention may be present in the form of the individual optical isomers, mixtures of the individual enantiomers, diastereomers or racemates, in the form of the tautomers and also in the form of the free bases or the corresponding acid addition salts with pharmacologically acceptable acids—such as for example acid addition salts with hydrohalic acids, for example hydrochloric or hydrobromic acid, or organic acids, such as for example oxalic, fumaric, diglycolic or methanesulphonic acid.

The substituent $R^1$ may denote a group selected from among hydrogen, $NH_2$, XH, preferably OH, halogen, preferably fluorine or chlorine and a $C_1$–$C_3$-alkyl group optionally substituted by one or more, preferably one, two or three halogen atoms, preferably fluorine or chlorine, preferably methyl or ethyl. Most preferably, the substituent $R^1$ is hydrogen.

The substituent $R^2$ may denote a group selected from among hydrogen, CHO, XH, preferably OH, —X—$C_1$–$C_2$-alkyl, preferably —O—$CH_3$ or —O—$CH_2CH_3$, and an optionally substituted $C_1$–$C_3$-alkyl group, while the alkyl group preferably consists of 1 to 2 carbon atoms, particularly preferably a carbon atom and may optionally be substituted, preferably by halogen atoms, most preferably by fluorine atoms. In particular, the substituent $R^2$ denotes methyl.

The substituents $R^3$ and $R^4$ may be identical or different and may represent a group selected from among optionally substituted $C_1$–$C_{10}$-alkyl, preferably $C_1$–$C_6$-alkyl, preferably $C_1$–$C_4$-alkyl, most preferably methyl, ethyl or propyl, particularly preferably methyl or ethyl, $C_2$–$C_{10}$-alkenyl, preferably ethenyl or propenyl, preferably ethenyl, $C_2$–$C_{10}$-alkynyl, preferably ethynyl or propynyl, aryl, preferably optionally substituted phenyl, heteroaryl, $C_3$–$C_8$-cycloalkyl, preferably cyclopropyl and cyclobutyl, $C_3$–$C_8$-heterocycloalkyl, —X-aryl, —X-heteroaryl, —X-cycloalkyl, —X-heterocycloalkyl, —$NR^8$-aryl, —$NR^8$-heteroaryl, —$NR^8$-cycloalkyl and
—$NR^8$-heterocycloalkyl, or
a group selected from among hydrogen, halogen, $COXR^8$, $CON(R^8)_2$, $COR^8$ and
$XR^8$, preferably hydrogen, or
the groups $R^3$ and $R^4$ may together denote a 2- to 5-membered alkyl bridge, preferably an ethylene, propylene or butylene bridge, while the propylene or butylene bridge may contain 1 to 2 heteroatoms, preferably oxygen, nitrogen or sulphur, most preferably an ethylene bridge.

Most preferably, the substituent $R^3$ denotes methyl or ethyl. The substituent $R^4$ most preferably denotes hydrogen or methyl. Particularly preferred are compounds wherein $R^3$ and $R^4$ represent methyl.

All the groups mentioned in the definition of $R^3$ and $R^4$ may optionally be substituted.

The group $R^5$ may contain hydrogen or a group selected from among optionally substituted $C_1$–$C_{10}$-alkyl, for example $C_1$–$C_6$-alkyl-aryl or $C_1$–$C_6$-alkyl-heteroaryl, preferably $C_1$–$C_6$-alkyl, most preferably $C_1$–$C_5$-alkyl, particularly preferably propyl, butyl, pentyl, hexyl, —$CH_2$-cyclohexyl, $(CH_2)_{1-2}$ cyclopropyl or $(CH_2)_4$—$OCOCH_3$, $C_2$–$C_{10}$-alkenyl, preferably propenyl, butenyl, pentenyl or hexenyl, preferably propenyl or hexenyl, $C_2$–$C_{10}$-alkynyl, preferably propynyl, butynyl or pentynyl, preferably propynyl, aryl, preferably phenyl, heteroaryl, —$C_3$–$C_6$-cycloalkyl, preferably cyclopropyl, cyclobutyl, cyclopentyl or cyclohexyl and —$C_3$–$C_6$-cycloalkenyl, preferably cyclohexenyl or cyclopentenyl, or the substituents $R^3$ and $R^5$ or $R^4$ and $R^5$ together denote a saturated or unsaturated $C_3$–$C_4$-alkyl bridge which may contain 1 to 2 heteroatoms, preferably oxygen, sulphur or nitrogen.

All the groups mentioned in the definition of $R^5$ may optionally be substituted.

The substituent $R^6$ may denote optionally substituted aryl, or heteroaryl, preferably aryl, preferably phenyl.

Most preferably, the substituent $R^6$ denotes a phenyl group, which may be substituted by one of the groups $R^9$ and $R^{10}$ described hereinafter, while the phenyl ring may carry one of the groups $R^9$, preferably in the para position, and one, two, three or four, preferably one or two, of the groups $R^{10}$, preferably in the ortho or meta position.

The substituent $R^7$ may denote hydrogen or —CO—X—$C_1$–$C_4$-alkyl, preferably hydrogen.

X denotes, in each case independently of one another, O or S, preferably O.

The groups $R^8$ mentioned in the definitions of the substituents $R^3$ and $R^4$ represent, independently of one another in each case, hydrogen or a group selected from among optionally substituted $C_1$–$C_4$-alkyl, $C_2$–$C_4$-alkenyl, $C_2$–$C_4$-alkynyl and phenyl, preferably hydrogen or $C_1$–$C_2$-alkyl.

The substituent $R^9$ may represent a group selected from among optionally substituted $C_1$–$C_6$-alkyl, preferably $C_1$–$C_4$-alkyl, preferably methyl, ethyl or propyl, most preferably methyl, $C_2$–$C_6$-alkenyl, $C_2C_6$-alkynyl, —CONH—$C_1$–$C_{10}$-alkylene, preferably —CONH—$C_1$–$C_3$-alkylene, preferably —CONH—$C_1$–$C_2$-alkylene, —O-aryl, preferably O—$C_6$–$C_{10}$-aryl, most preferably O-phenyl, —O-heteroaryl, —O-cycloalkyl, preferably O—$C_3$–$C_6$-cycloalkyl, most preferably O-cyclopropyl, —O-heterocycloalkyl, aryl, preferably $C_6$–$C_{10}$-aryl, most preferably phenyl, heteroaryl, cycloalkyl, preferably $C_3$–$C_6$-cycloalkyl, most preferably cyclopropyl, and heterocycloalkyl, or a group selected from among —O—$C_{1-6}$-alkyl-$Q^1$, —$CONR^8$—$C_1$–$C_{10}$-alkyl-$Q^1$, —$CONR^8$—$C_1$–$C_{10}$-alkenyl-$Q^1$, —$CONR^8$—$Q^2$, halogen, for example fluorine, chlorine, bromine or iodine, OH, —$SO_2R^8$, —$SO_2N(R^8)_2$, —$COR^8$, —$COOR^8$, —$N(R^8)_2$, —$NHCOR^8$, $CONR^8OC_1$–$C_{10}$-alkyl$Q^1$ and $CONR^8OQ^2$, where $Q^1$ and $Q^2$ are as hereinbefore defined.

Preferably, $R^9$ denotes one of the following groups —CONH—$C_1$–$C_{10}$-alkyl, preferably —CONH—$C_1$–$C_3$-alkyl, most preferably —CONH—$C_1$–$C_2$-alkyl, while this alkyl may itself optionally be substituted, by CN, optionally substituted aryl, preferably optionally substituted phenyl, heteroaryl, preferably thienyl, thiazolyl, imidazolyl, pyridyl, pyrimidyl or pyrazinyl, saturated or unsaturated heterocycloalkyl, preferably pyrazolyl, pyrrolidinyl, piperidinyl, piperazinyl or tetrahydro-oxazinyl, an amine group, preferably methylamine, benzylamine, phenylamine or heteroarylamine, saturated or unsaturated bicyclic ring systems, preferably benzimidazolyl and cycloalkyl, preferably cyclohexyl. Moreover $R^9$ preferably denotes —CONH-heteroaryl, preferably —CONH-pyridyl, —CONH—$C_3$–$C_{10}$-cycloalkyl, preferably —CONH-cyclopropyl —CONH-cyclobutyl or —CONH-cyclopentyl, most preferably —CONH-cyclopropyl; —CONH—$C_3$–$C_{10}$-heterocycloalkyl , —CONH—$C_6$–$C_{10}$-aryl, preferably —CONH-phenyl, COO—$C_1$–$C_3$-alkyl, most preferably $COOCH_3$, COOH, halogen, preferably F or chlorine, OH or a group of formula

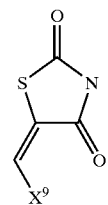

All the groups mentioned in the definition of $R^9$ may optionally be substituted, preferably by one or more of the groups selected from among OH, $OCH_3$, Cl, F, $CH_3$, COOH, $CONHCH_2Ph$ and $CONHCH_2$-pyrazinyl-$CH_3$.

The substituent $R^{10}$ may be identical or different in each case and may denote a group selected from among optionally substituted $C_1$–$C_6$-alkyl, preferably $C_1$–$C_3$-alkyl, $C_2$–$C_6$-alkenyl, preferably $C_2$–$C_3$-alkenyl and $C_2$–$C_6$-alkynyl, preferably $C_2$–$C_3$-alkynyl, —O—$C_1$–$C_6$-alkyl, preferably —O—$C_1$–$C_3$-alkyl, —O—$C_2$–$C_6$-alkenyl, —O—$C_2C_6$-alkynyl, $C_3$–$C_6$-heterocycloalkyl and $C_3$–$C_6$-cycloalkyl, or a group selected from among hydrogen, —$CONH_2$, —$COOR^8$, —$OCON(R^8)_2$, —$N(R^8)_2$, —$NHCOR^8$, —$NHCON(R^8)_2$, —$NO_2$ and halogen, for example fluorine, chlorine, bromine or iodine.

Preferably, the substituent $R^{10}$ denotes hydrogen, methyl, methoxy, fluorine or chlorine, most preferably hydrogen or methoxy, particularly preferably methoxy.

Adjacent groups $R^9$ and $R^{10}$ may together denote a bridge of general formula

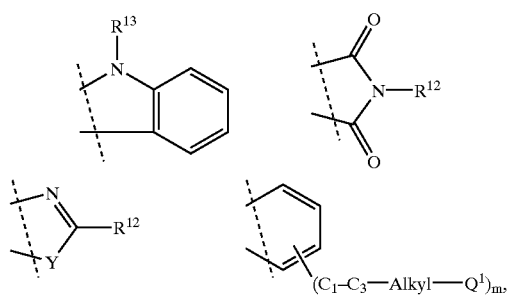

wherein

Y denotes O, S or $NR^{11}$, preferably $NR^{11}$, m denotes 0, 1 or 2, preferably 1, $R^{11}$ denotes hydrogen or $C_1$–$C_2$-alkyl, preferably hydrogen or methyl, most preferably hydrogen, $R^{12}$ denotes hydrogen or a group selected from among optionally substituted phenyl, pyridyl, pyrazinyl, pyrimidinyl, pyridazinyl, —$C_1$–$C_3$-alkyl-phenyl, —$C_1$–$C_3$-alkyl-pyridyl, —$C_1$–$C_3$-alkyl-pyrazinyl, —$C_1$–$C_3$-alkyl-pyrimidinyl and —$C_1$–$C_3$-alkyl-pyridazinyl, preferably phenyl, pyridyl and pyrazinyl, and $R^{13}$ denotes $C_1$–$C_6$-alkyl, preferably methyl or ethyl.

The compounds according to the invention may be prepared by synthesis methods A and B described hereinafter, while the substituents of general formulae (A1) to (A6) have the meanings given hereinbefore. These methods are to be understood as illustrations of the invention without restricting it to their subject matter.

Method A

Step 1A

A compound of formula (A1) is reacted with a compound of formula (A2) to obtain a compound of formula (A3) (Diagram 1A). This reaction may be carried out according to WO 0043369 or WO 0043372. Compound (A1) is commercially obtainable, for example, from City Chemical LLC, 139 Allings Crossing Road, West Haven, Conn., 06516, USA. Compound (A2) may be prepared by procedures known from the literature: (a) F. Effenberger, U. Burkhart, J. Willfahrt Liebigs *Ann. Chem.* 1986, 314–333; b) T. Fukuyama, C.-K. Jow, M. Cheung, *Tetrahedron Lett.* 1995, 36, 6373–6374; c) R. K. Olsen, *J. Org. Chem.* 1970, 35, 1912–1915; d) F. E. Dutton, B. H. Byung *Tetrahedron Lett.* 1998, 30, 5313–5316; e) J. M. Ranajuhi, M. M. Joullie *Synth. Commun.* 1996, 26, 1379–1384.).

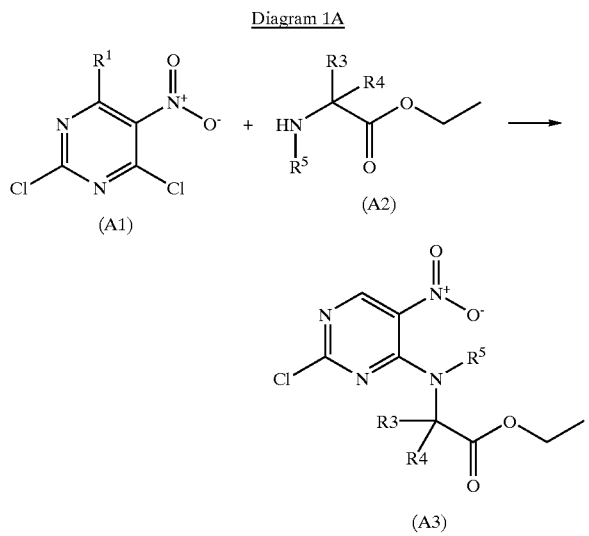

Diagram 1A

In Step 1 A, 1 equivalent of the compound (A1) and 1 to 1.5 equivalents, preferably 1.1 equivalents of a base, preferably potassium carbonate, potassium hydrogen carbonate, sodium carbonate or sodium hydrogen carbonate, calcium carbonate, most preferably potassium carbonate, are stirred in a diluent, for example acetone, aqueous acetone, tetrahydrofuran, diethylether or dioxane, preferably acetone or diethylether, most preferably acetone.

At a temperature of 0 to 15° C., preferably 5 to 10° C., 1 equivalent of an amino acid of formula (A2), dissolved in an organic solvent, for example acetone, tetrahydrofuran, diethylether or dioxane, preferably acetone, is added dropwise. The reaction mixture is heated to a temperature of 18° C. to 30° C., preferably about 22° C., with stirring and then stirred for a further 10 to 24 hours, preferably about 12 hours. Then the diluent is distilled off, the residue is combined with water and the mixture is extracted two to three times with an organic solvent, such as diethylether or ethyl acetate, preferably ethyl acetate. The combined organic extracts are dried and the solvent is distilled off. The residue (compound A3) may be used in Step 2 without any prior purification.

Step 2A

The compound obtained in Step 1A (A3) is reduced at the nitro group and cyclised to form the compound of formula (A4) (Diagram 2A).

Diagram 2A

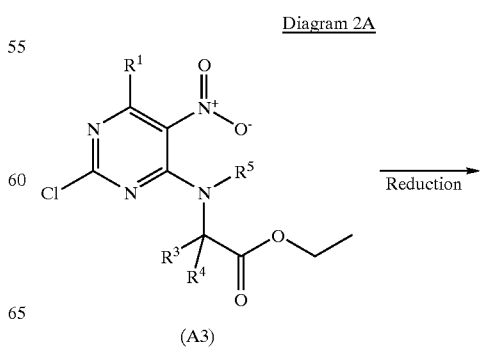

-continued

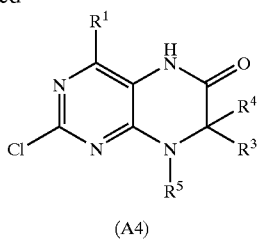

(A4)

In Step 2A, 1 equivalent of the nitro compound (A3) is dissolved in an acid, preferably glacial acetic acid, formic acid or hydrochloric acid, preferably glacial acetic acid, and heated to 50 to 70° C., preferably about 60° C. Then a reducing agent, for example zinc, tin or iron, preferably iron filings, is added to complete the exothermic reaction and the mixture is stirred for 0.2 to 2 hours, preferably 0.5 hours, at 100 to 125° C., preferably at about 117° C. After cooling to ambient temperature the iron salt is filtered off and the solvent is distilled off. The residue is taken up in a solvent or mixture of solvents, for example ethyl acetate or dichloromethane/methanol 9/1 and semisaturated NaCl solution, and filtered through kieselgur, for example. The organic phase is dried and evaporated down. The residue (compound (A4)) may be purified by chromatography or by crystallisation or used as the crude product in Step 3A of the synthesis.

Step 3A

The compound obtained in Step 2A (A4) may be reacted by electrophilic substitution as shown in Diagram 3A to obtain the compound of formula (A5).

Diagram 3A

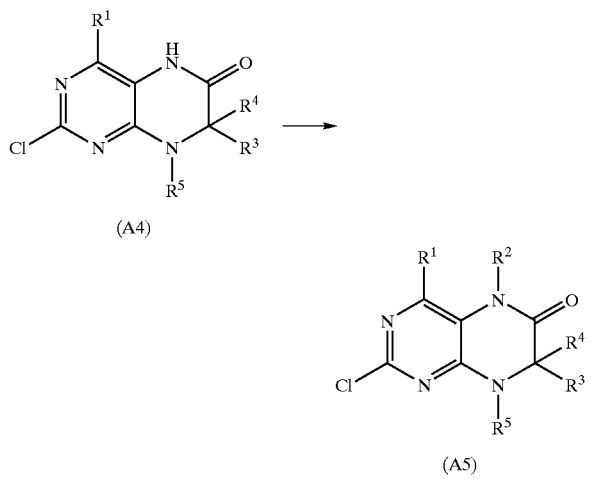

In Step 3A 1 equivalent of the amide of formula (A4) is dissolved in an organic solvent, for example dimethylformamide or dimethylacetamide, preferably dimethylacetamide, and cooled to about −5 to 5° C., preferably 0° C. Then 0.9 to 1.3 equivalents of sodium hydride and 0.9 to 1.3 equivalents of alkyl halide, for example methyl iodide, are added. The reaction mixture is stirred for 0.1–3 hours, preferably about 1 hour, at about 0 to 10° C., preferably at about 5° C., and may optionally be left to stand for a further 12 hours at this temperature. The reaction mixture is evaporated down and extracted with water and an organic solvent, preferably dichloromethane or ethyl acetate. The organic phases are evaporated down. The residue (compound (A5)) may be purified by chromatography, preferably over silica gel.

Step 4A

The amination of the compound (A5) obtained in Step 3A to yield the compound of formula (A7) (Diagram 4A) may be carried out using the methods known from the literature of variants 4.1 A (a) M. P. V. Boarland, J. F. W. McOmie *J. Chem. Soc.* 1951, 1218 . 1221; b) F. H. S. Curd, F. C. Rose *J. Chem. Soc.* 1946, 343–348., 4.2 A (a) Banks *J. Am. Chem. Soc.* 1944, 66,1131 b) Ghosh and Dolly *J. Indian Chem. Soc.* 1981, 58, 512–513.

Diagram 4A

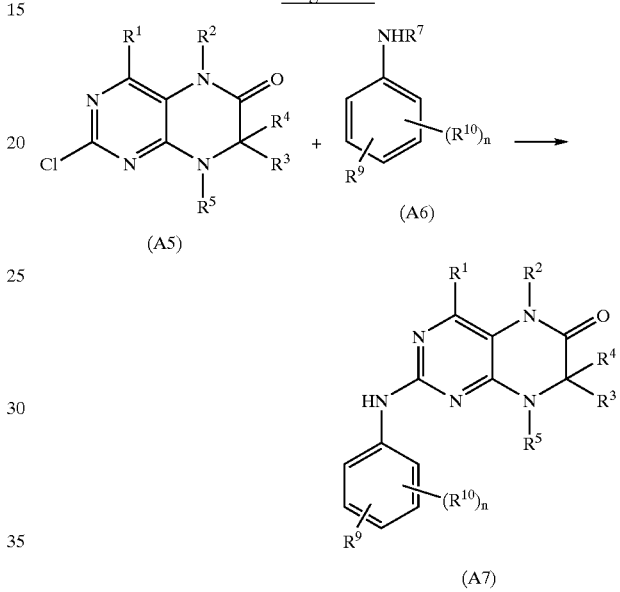

For example, in variant 4.1A, 1 equivalent of the compound (A5) and 1 to 3 equivalents, preferably about 2 equivalents of the compound (A6) are heated without a solvent or in an organic solvent such as for example sulpholane, dimethylformamide, dimethylacetamide, toluene, N-methylpyrrolidone, dimethylsulphoxide or dioxane, preferably sulpholane, for 0.1 to 4 hours, preferably 1 hour, at 100 to 220° C., preferably at about 160° C. After cooling, the product (A7) is crystallised by the addition of organic solvents or mixtures of solvents, e.g. diethylether/methanol, ethyl acetate, methylene chloride, or diethylether, preferably diethylether/methanol 9/1, or purified by chromatography.

For example, in variant 4.2A, 1 equivalent of the compound (A5) and 1 to 3 equivalents of the compound (A6) are stirred with acid, for example 1–10 equivalents of 10–38% hydrochloric acid and/or an alcohol, for example ethanol, propanol, butanol, preferably ethanol, at reflux temperature for 1 to 48 hours, preferably about 5 hours.

The product precipitated (A7) is filtered off and optionally washed with water, dried and crystallised from a suitable organic solvent.

If $R^6$ denotes an optionally substituted benzimidazole, the preparation of the compounds (A6) using methods known from the literature may be carried out as shown in the following diagram, for example:

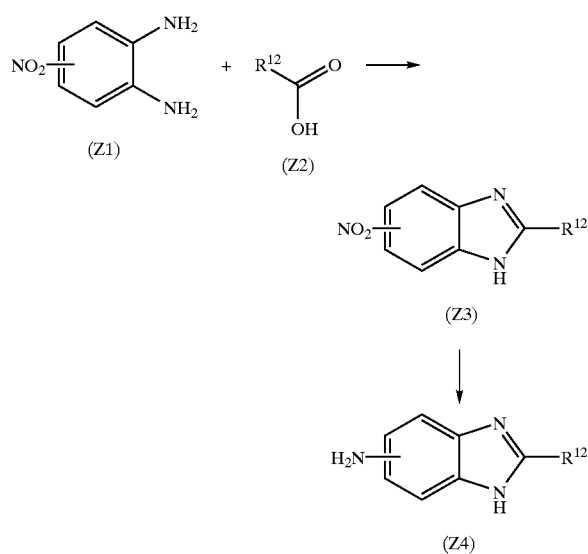

Accordingly, for example, 33 mmol of the compound (Z1), 49 mmol of the compound (Z2) and 49 mmol of 1-ethoxycarbonyl-2-ethoxydihydroquinoline (EEDQ) are stirred into 50 ml of an organic solvent, preferably dimethylformamide, at about 100 to 130° C., preferably at about 115° C., 1 to 4 hours, preferably about 3 hours. Then the cooled reaction solution is added to 50 to 400 ml, preferably about 200 ml of a water/ethyl acetate mixture (mixing ratio about 1:1). The crystals formed (Z3) are suction filtered and washed.

Then 4.2 mmol of the compound (Z3) are stirred with 12.5 mmol of tin(II)chloride and 30 mmol of potassium carbonate in about 50 ml of an organic diluent, preferably ethyl acetate, at about 22° C. for 4 to 48 hours, preferably about 24 hours. After the addition of 22 g of kieselgur the mixture is extracted with an organic diluent or mixture of diluents, preferably with a mixture of dichloromethane/methanol (9:1), the combined extracts are evaporated down and the precipitate formed (Z4) or the crystals produced (Z4) is or are isolated.

Step 5A

If $R^9$ denotes —CONR$^8$—C$_1$–C$_{10}$-alkyl-Q$^1$, —CONH—C$_1$–C$_5$-alkylene or —CONR$^8$—Q$^2$, wherein the substituents have the meanings given hereinbefore, the compounds according to the invention may be prepared using methods known from the literature, for example as shown in Diagram 5A.

The compound (A7') obtained in Step 4A may be reacted either by saponification and subsequent amination to obtain the amide of general formula (A10) (Diagram (5A) variant 5.1A), or by saponification, with subsequent conversion into the acid chloride (A9) and subsequent amination (Diagram (5A) variant 5.2A).

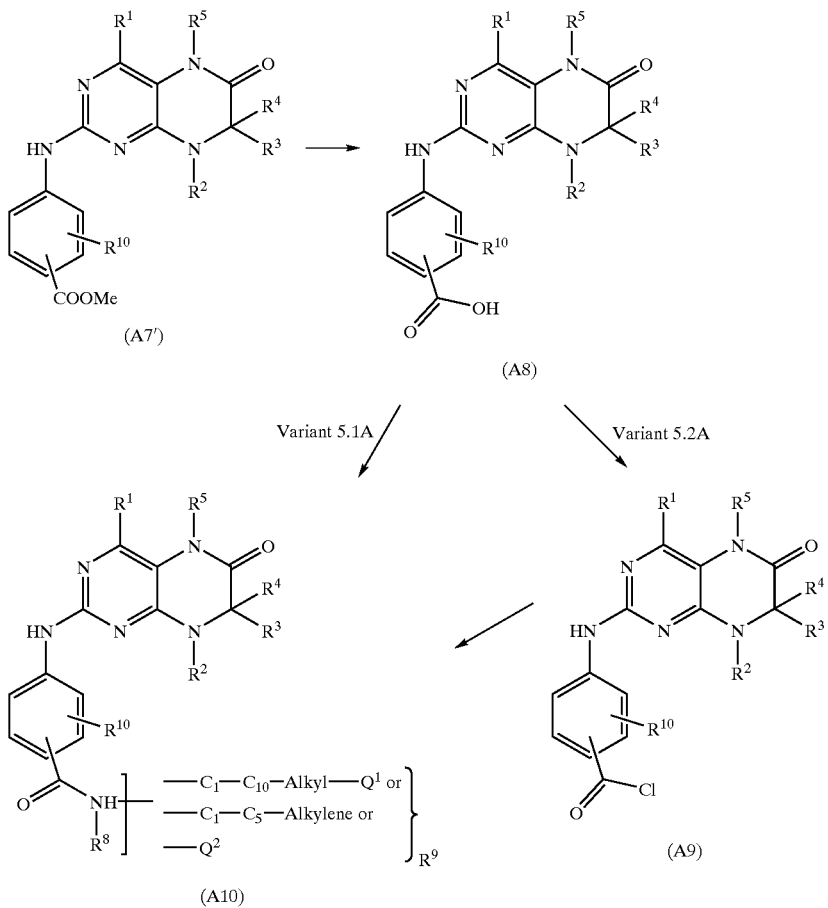

Diagram 5A

Variant 5.1A:

In variant 5.1A, for example, 20 mmol of the ester (A7') are heated in about 100 ml of a base, preferably 1N sodium hydroxide solution or lithium hydroxide solution and about 500 ml of an alcohol, for example with ethanol, dioxane or methanol, preferably methanol, until the ester is completely reacted. Then the alcohol is distilled off. The residue is taken up in about 200 ml of water and acidified while cooling with acid, for example hydrochloric acid, preferably with 2 N hydrochloric acid. The product (A8) is filtered off and dried.

For example, about 0.5 mmol of the compound (A8) are dissolved with about 0.5 mmol of O-benzotriazolyl-N,N,N', N'-tetramethyluronium tetrafluoroborate (TBTU) and about 1.4 mmol of diisopropylethylamine (DIPEA) in about 5 ml of an organic diluent, for example tetrahydrofuran, dimethylformamide, N-methylpyrrolidone, dimethylacetamide, preferably dimethylformamide. After the addition of about 0.75 mmol of an amine which forms the substituent $R^9$, the reaction mixture is stirred for 0.1 to 24 hours, preferably about 12 hours at 20° C. to 100° C. The product of formula (A10) is obtained for example by crystallisation or chromatographic purification.

Variant 5.2A:

In variant 5.2A about 1 mmol of the acid (A8) for example is suspended in about 2.7 ml of thionyl chloride. The mixture is heated to 40° C. to 80°C., preferably about 50° C., and at constant temperature 2 to 10 drops, preferably about 3 drops of dimethylformamide are added to the reaction mixture with stirring. Then stirring is continued at 90° C. until the reaction is complete. Excess thionyl chloride is distilled off. About 1 mmol of the acid chloride formed (A9) are dissolved in about 30 ml of an organic diluent, for example dichloromethane. After the addition of an amine which forms the substituent $R^9$ the mixture is stirred at about 22° C. The precipitate formed is filtered off and washed with water. The residue remaining is washed with an organic diluent, for example methanol. The mother liquor is purified, for example by chromatography, and evaporated down. The product (A10) remains.

Method B

Alternatively to the methods described above, after Step 1A first the compound (A3) may be aminated and then the product (B1) may be cyclised to yield the compound (B2), as shown in Diagram B. Further substitution of the compound (B2) to yield the compound (A7) may be carried out for example as in Step 3A.

Diagram B

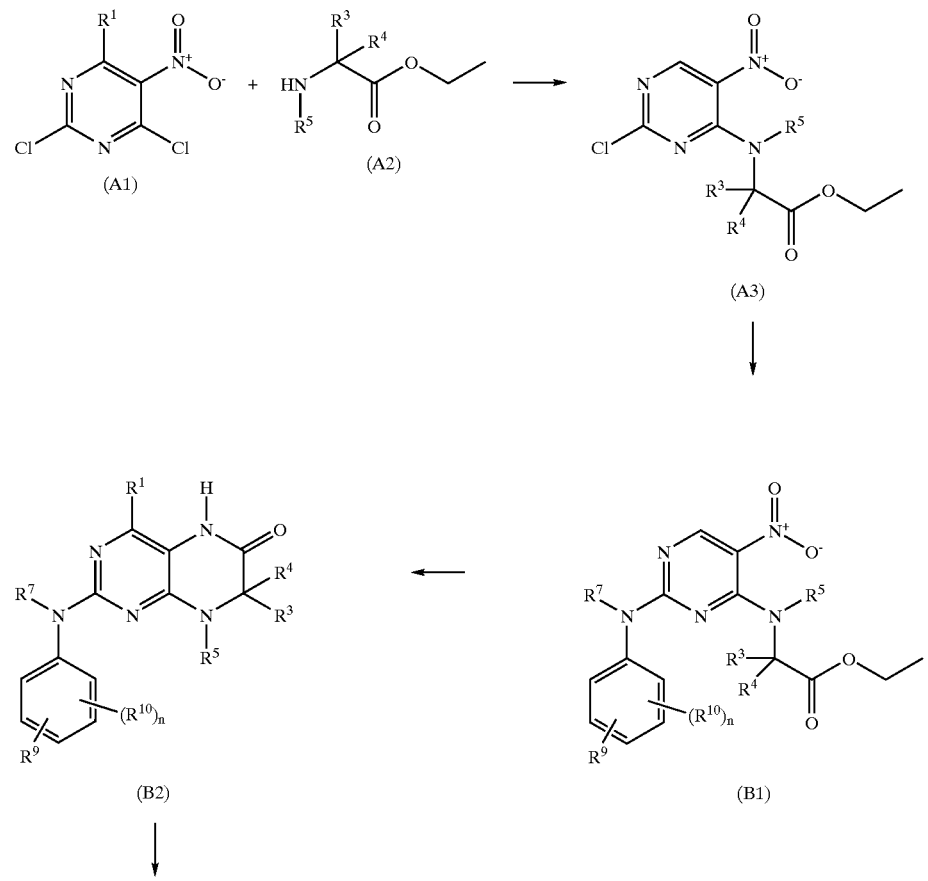

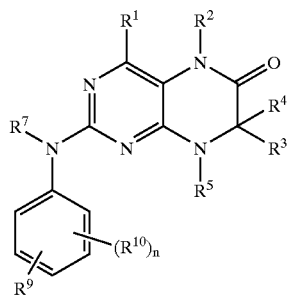

(A7)

The new compounds of general formula (I) may be synthesised analogously to the following examples of synthesis. These Examples are, however, intended only as examples of procedures to illustrate the invention further, without restricting the invention to their subject matter.

EXAMPLE 63 AND EXAMPLE 109

In order to synthesise the compounds 63 and 109, first an intermediate compound 4

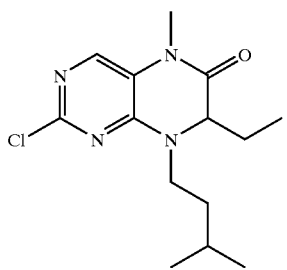

4 is prepared as described hereinafter.

38.9 ml (0.263 mol) of ethyl 2-bromobutyrate and 36.4 g (0.263 mol) of potassium is carbonate were placed in 350 ml of ethyl acetate, and then 46.7 ml (0.402 mol) of isoamylamine, dissolved in 70 ml of ethyl acetate, were rapidly added dropwise. The mixture was refluxed for 20 h. The salt formed was filtered off, the filtrate was concentrated by evaporation, combined with 50 ml of toluene and again evaporated to dryness.

Yield: 54.3 g of a compound 1 (red oil).

54.3 g of compound 1, dissolved in 400 ml acetone, and 30.7 g (0.222 mol) of potassium carbonate were cooled to 8° C. with stirring, combined with a solution of 43.1 g (0.222 mol) of 2,4-dichloro-5-nitropyrimidine in 250 ml acetone and then stirred for 24 h at RT.

The suspension formed was concentrated by evaporation, the residue was extracted with water and ethyl acetate, the organic phase was washed with water and NaCl solution, dried over $MgSO_4$ and evaporated to dryness.

Yield: 87.3 g of a compound 2 (brown oil).

44.1 g of compound 2 were dissolved in 800 ml glacial acetic acid and heated to 65° C. and 36 g of iron filings were added batchwise. Then the mixture was stirred for 3 h at 70° C., the precipitate was filtered off and the filtrate was concentrated by evaporation.

The residue was applied to silica gel in dichloromethane/methanol 90:10, concentrated by evaporation and purified by column chromatography (eluant: ethyl acetate/cyclohexane 1:1).

The residue was precipitated from ethyl acetate/petroleum ether.

Yield: 16.1 g of a compound 3 (beige powder).

16.1 g of compound 3 were dissolved in 75 ml of dimethylacetamide and cooled to 5° C. under a nitrogen atmosphere with stirring. Then 2.51 g (0.063 mol) of NaH, 60% dispersion in mineral oil, was added, whereupon the temperature temporarily rose to 16° C. After 30 minutes 3.94 ml (0.063 mol) of methyl iodide, dissolved in 75 ml dimethylacetamide, were added, and the mixture was stirred for 24 h at 22° C.

The solvent was concentrated by evaporation, combined with 200 ml of water and the precipitate formed was suction filtered, then extracted by stirring with petroleum ether.

Yield: 15.1 g of a compound 4 (yellow powder).

$^1$H-NMR (250 MHz):=7.80 (1H, s), 4.35 (m, 1H), 3.92 (m, 1H), 3.22 (s, 3H), 3.14 (m, 1H), 1.81 (m, 2H), 1.60–1.40 (m, 3H), 0.90 (m, 6H), 0.70 (t, 3H).

SYNTHESIS OF EXAMPLE 63

2.5 g of compound 4, 1.43 g of 4-amino-3-methoxybenzoic acid, 1.25 mL of conc. hydrochloric acid, 150 mL of dist. water and 37.5 mL of ethanol were refluxed for 10 h. The precipitate was filtered off, washed with water and extracted by stirring in methanol. Then the precipitate was recrystallised using petroleum ether and ether.

Yield: 1.6 g of a compound 5 (white powder).

0.2 g of compound 5, 5 mL of benzylamine, 0.16 g of TBTU, 0.17 g of DIPEA were dissolved in 2 ml of dimethylformamide (DMF) and stirred for 48 h at ambient temperature. Then the reaction mixture was taken up in methylene chloride, washed with water and the organic phase was evaporated down. When petroleum ether/ethyl acetate 9:1 was added the product was precipitated in the form of light beige crystals.

Yield: 0.18 g. Melting point: 178° C.

SYNTHESIS OF EXAMPLE 109

5 g of 2 amino-5-nitroaniline, 6.03 g of 4-pyridylcarboxylic acid, 12.1 g of EEDQ are dissolved in 50 mL of DMF and stirred at 115° C. for 1.75 h, then the DMF is distilled off in vacuo and the reaction mixture is then heated to 180° C. for 1 h. The residue is taken up in 30 mL of DMF and combined with 200 mL of water and 100 mL of ethyl acetate. The crystal slurry obtained is filtered off and washed with water, ethyl acetate and ether.

Yield: 5.8 g of a compound 6.

2 g of the compound 6 is combined with 0.2 g of 5% Pd/C in 30 mL of ethanol and hydrogenated in the presence of hydrogen. It is then evaporated down and crystallised from ethanol and toluene.

Yield: 1.75 g of white powder of a compound 7.

0.2 g of the compound 5, 0.28 g of the compound 7, 0.001 g of sodium-tert. butoxide, 2.5 mL of ethyleneglycol dimethylether, 0.006 g of palladium(II) acetate and 0.22 g of 2-(di-tert.-butylphospino)biphenyl are dissolved in 1.5 mL of N-methylpyrrolidone (NMP). Then the mixture is heated to 160° C. for 0.5 h. The reaction mixture is then purified over 20 g of silica gel and the product is crystallised from ether, ethyl acetate and petroleum ether.

Yield: 0.04 g of yellow crystals. Melting point: 180° C.

EXAMPLE 218, 58 AND 4

In order to synthesise the compounds 218, 58 and 4, first an intermediate compound 11

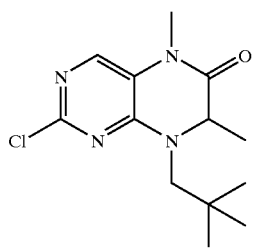

11 is prepared as described hereinafter.

55.8 g of DL-alanine methyl ester×HCl were dissolved in 500 ml of methanol, then 76.1 ml of 30% sodium methoxide solution was added and the salt was filtered off. 37.8 g of trimethylacetaldehyde were added to the filtrate, then it was left to stand for 22 h. Then 9.5 g of 10% Pd/C was added and the mixture was hydrogenated for 3.1 h at 0.5 bar and 20° C. The reaction mixture was suction filtered through kieselgur and concentrated by evaporation. The residue was taken up in diethylether, the salts were filtered through kieselgur and the filtrate was concentrated by evaporation.

Yield: 55.8 g of a compound 8 (clear liquid).

48.5 g of 2,4-dichloro-5-nitropyrimidine were placed in 400 ml of diethylether, 41.0 g of potassium hydrogen carbonate in 400 ml of water were added, and the mixture was cooled to −5° C. 43.3 g of compound 8 were dissolved in 400 ml of diethylether and added dropwise at −5° C. The mixture was stirred for 1 h at −5° C. and for 2 h at 0° C., then heated to ambient temperature and the reaction mixture was left to stand for 24 h.

The organic phase was separated off, dried over MgSO$_4$ and evaporated to dryness.

Yield: 79.2 g of a compound 9 (yellow resin).

79.0 g of compound 9 were dissolved in 1000 ml of glacial acetic acid and heated to 70° C. After the removal of the heat source 52 g of iron was added batchwise. The temperature rose to about 110° C. and the mixture was stirred for 1 h at this temperature. The suspension was filtered while hot and the filtrate was concentrated by evaporation.

The residue was taken up in ethyl acetate and combined with 150 ml of conc. HCl, the organic phase was separated off and the aqueous phase extracted several times with dichloromethane. The combined organic phases were concentrated by evaporation, applied to silica gel and purified by column chromatography (eluant: petroleum ether/ethyl acetate 1:1).

As the isolated substance was still highly contaminated, it was again purified over silica gel. The desired compound crystallised out, the crystals were suction filtered. The mother liquor was concentrated by evaporation and recrystallised from ethyl acetate/diethylether.

Yield: 17.63 g of a compound 10.

7.6 g of the compound 10 and 6.4 ml of methyl iodide were placed in 75 ml of dimethylacetamide (DMA) and cooled to −15° C. 1.25 g of NaH, 60% dispersion in mineral oil, was added batchwise, and stirred for 30 min. at −10° to −5° C. Then 150 ml of ice water were added, the crystals were suction filtered and washed with water and petroleum ether. The crystals were taken up in dichloromethane, filtered through kieselgur and the filtrate was evaporated to dryness. It was recrystallised from petroleum ether.

Yield: 6.3 g of compound 11 (beige crystals).

$^1$H-NMR (250 MHz):=7.73 (1H, s), 4.35 (d, 1H), 4.25 (m, 1H), 3.35 (s, 3H), 2.55 (d, 1H), 1.31 (d, 3H), 0.95 (s, 9H).

SYNTHESIS OF EXAMPLE 218

0.2 g of compound 11, 3,5-difluoro-4-hydroxyaniline and 0.75 mL of sulpholane were heated to 130° C. for 15 min, to 140° C. for 15 min and to 170° C. for 10 min. Then the mixture was combined with ether, the supernatant solution was decanted off and the residue was crystallised from methanol/ether and recrystallised again from methanol.

Yield: 0.15 g of white crystals. Melting point:>250° C.

SYNTHESIS OF EXAMPLE 4

6.3 g of compound 11 were dissolved in 25 mL of sulpholane at 100° C., then combined with 4.0 g of ethyl 4-aminobenzoate and heated to 170° C. for 1 h. Then the mixture was combined with 50 mL of ether. After crystallisation started, a further 50 mL of ether and 50 mL of methanol were added. The crystals were recrystallised from methanol.

Yield: 6.6 g of a compound 12 (yellowish crystals), melting point: from 65° C. decomposition sets in.

3.55 g of compound 12 were suspended in 250 mL of methanol and at 60° C. combined with 25 mL of 4 N sodium hydroxide solution. After 6 h, 15 mL of glacial acetic acid were added, the resulting crystals were filtered off and washed with methanol/ether.

Yield: 1.2 g of a compound 13 (white crystals).

1.5 g of compound 13 were dissolved in 7.5 mL of thionyl chloride and heated to 80° C. for 1 h. Then the thionyl chloride was eliminated by distillation, the residue was stirred with ether, the crystals were suction filtered and washed with ether.

Yield: 1.7 g of a compound 14 (yellow crystals).

0.18 g of 3-aminopyridine were dissolved in 10 mL of tetrahydrofuran (THF) and combined with 0.4 mL of triethylamine. Then 0.22 g of compound 14 were added and the mixture was stirred for 16 h at ambient temperature. The mixture was evaporated to dryness, taken up in ethyl acetate, extracted with water, evaporated down again and the product was crystallised from ethyl acetate.

Yield: 0.07 g (beige crystals), Melting point: 215–216° C.

SYNTHESIS OF EXAMPLE 58

0.05 g of compound 13 were suspended in 10 mL of dichloromethane, then combined with 0.15 mL of DIPEA and 0.05 g of TBTU. The solution was then stirred for 30 min and combined with 0.01 mL of 4-picolylamine. After 18 h the mixture was combined with 20 mL of water, the organic phase was separated off and the product was purified by silica gel chromatography, then recrystallised from ethyl acetate/petroleum ether.

Yield: 0.044 g (white crystals), Melting point: 238–240° C.

EXAMPLES 65 AND 125

In order to synthesise the compounds 65 and 125, first an intermediate compound 18

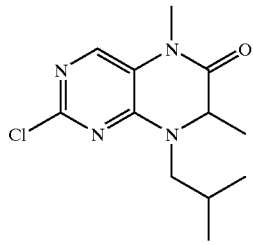

18 is prepared as described hereinafter.

28.3 g of isobutylamine, 36 g of ethyl R,S-2-bromopropionate and 28 g of potassium carbonate were refluxed in 150 ml of ethyl acetate for 6 h. After cooling the salt was suction filtered, the mother liquor was concentrated by evaporation.

The residue was combined with 100 ml of toluene and evaporated to dryness.

Yield: 37.2 g of a compound 15 (yellow oil).

38.4 g of 2,4-dichloro-5-nitropyrimidine were placed in 300 ml of diethylether, 30 g of potassium hydrogen carbonate in 300 ml of water were added and the mixture was cooled to 0° C. 37.0 g of compound 15 were dissolved in 300 ml of diethylether and added dropwise at 0°–3° C. After 3 h the phases were separated, the organic phase was dried and evaporated to dryness.

Yield: 71.6 g of a compound 16.

40.0 g of compound 16 were dissolved in 300 ml of glacial acetic acid and heated to 70° C. After removal of the heat source, 30 g of iron was added batchwise. The temperature rose to 110° C. The reaction mixture was cooled to 90° C. and stirred for 20 min. at this temperature. Then it was filtered while hot and the filtrate was concentrated by evaporation. The residue was stirred with 300 ml of water and 300 ml of dichloromethane and filtered through kieselgur. The phases were separated. The organic phase was washed with water, dried over $MgSO_4$ and is evaporated to dryness. It was extracted from petroleum ether.

Yield: 26.7 g of a compound 17.

15.0 g of compound 17 were placed in 100 ml of DMA, 4.13 ml of methyl iodide were added and the mixture was cooled to 5° C. 2.60 g of NaH were added batchwise as a 60% dispersion in mineral oil. The temperature rose to 13° C. After 30 min. 300 ml of ice water were added, the crystals precipitated were suction filtered and washed with petroleum ether.

Yield: 13.9 g of a compound 18.

$^1$H-NMR (250 MHz):=7.95 (1H, s), 4.30 (m, 1H), 3.95 (m, 1H), 3.24 (s, 3H), 2.95 (m, 1H), 2.05 (m, 1H), 1.30 (d, 3H), 0.96 (d, 3H), 0.92 (d, 3H).

SYNTHESIS OF EXAMPLE 65

2.1 g of compound 18 were combined with ethyl 4-aminobenzoate in 10 mL sulpholane and stirred for 2 h at 160° C. Then ether was added and the crystals precipitated were washed with ether:

Yield: 3.0 g of a compound 19.

3 g of the compound 19 were combined with 200 mL of methanol and 25 mL of 4N NaOH and stirred for 4 h at 60° C. Then glacial acetic acid was added, the crystals precipitated were filtered off and washed with ether.

Yield: 2.3 g of a compound 20 (white crystals).

0.1 g of compound 20 were suspended in 3 mL of dichloromethane and 3 mL of DMF, and then combined with 0.13 g of DIPEA, 0.095 g of TBTU and 0.045 g of hydroxybenzotriazole (HOBt). Then the solution was stirred for 30 min and combined with 0.035 g of N-methyl-3-picolylamine. After 0.5 h the mixture was combined with water and 1 g of potassium carbonate, the aqueous phase was extracted twice with 50 mL of ethyl acetate and the product was purified by silica gel chromatography and then recrystallised from ethanol/acetone.

Yield: 0.08 g.

SYNTHESIS OF EXAMPLE 125

3.7 g of compound 20, 3.8 g of TBTU, 1.6 g of HOBt, 5 mL of DIPEA were dissolved in 40 mL of DMF and stirred for 4 h at ambient temperature. The mixture was evaporated down, taken up in 200 mL of ethyl acetate and extracted twice with 5 mL of 5% potassium carbonate solution. The organic phase was evaporated down, the crystals precipitated were filtered off and washed with ethyl acetate and ether.

Yield: 1.65 g of a compound 21 (yellowish crystals).

0.486 g of compound 21 were refluxed with 0.33 g of 1,2-phenylenediamine in 10 mL of toluene for 0.5 h, then the mixture was evaporated down. The residue was combined with 100 mL ethyl acetate, the organic phase was extracted twice with water. The organic phase was evaporated down, the crystals precipitated were suction filtered and washed with a little ethyl acetate.

Yield: 0.25 g of a compound 22 (white crystals).

0.22 g of compound 22 were stirred into 20 g of polyphosphoric acid for 0.5 h at 150° C., then the mixture was poured onto ice and ammonia was added. It was then extracted twice with 100 mL of ethyl acetate, the organic phase was washed with water and evaporated down. The precipitated product (crystals) was suction filtered and washed with ethyl acetate and ether.

Yield: 0.115 g of yellowish crystals, Melting point: 287° C. (decomposition).

EXAMPLE 171

In order to synthesise compound 171 first an intermediate compound 27 [sic]

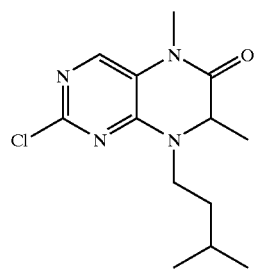

27

34.4 g of N-isopentyl-benzylamine, 36.2 g of ethyl 2-bromo-propionate and 42.0 g of potassium carbonate were placed in 250 ml of DMF and stirred for 3 h at 110° C. After cooling the inorganic salts were filtered off, the filtrate was concentrated by evaporation. The residue was extracted with water and diethylether, the organic phase was washed with water, dried and evaporated to dryness.

Yield: 55.5 g of a compound 23.

55.5 g of compound 23 were placed in 600 ml of ethanol, and hydrogenated with 20 ml of 32% HCl and 6 g of 10%

Pd/C at 20° C. under 5 bar for 20 min. Then it was filtered through kieselgur and concentrated by evaporation. The residue was combined with 400 ml of diethylether, the precipitate was suction filtered and washed with diethylether.

Yield: 23.5 g of a compound 24, melting point 105° C.

23.5 g of compound 24 were dissolved in 200 ml of water and combined with 20.0 g (0.103 mol) of 2,4-dichloro-5-nitropyrimidine in 400 ml of diethylether. After the reaction mixture had been cooled to −10° C., 50.0 g (0.499 mol) of potassium carbonate were added batchwise. The mixture was stirred at −5° C. for 1 h and at 0° C. for 1 h, then heated to ambient temperature. The aqueous phase was separated off, the organic phase was washed with water, dried and evaporated to dryness.

Yield: 36.9 g of a compound 25.

20.0 g of the compound 25 were dissolved in 280 ml of glacial acetic acid and heated to 70° C. After removal of the heat source 17 g of iron were added. The temperature rose to 100° C., then the mixture was stirred for 30 min. at this temperature.

It was then filtered while hot and the filtrate was concentrated by evaporation. The residue was combined with 300 ml of dichloromethane and 30 ml of 32% HCl, the phases were separated, the aqueous phase was extracted with dichloromethane, the combined organic phases were washed with water and aqueous ammonia solution, dried and evaporated to dryness. The residue was extracted with diethylether.

Yield: 10.5 g of a compound 26, melting point: 182°–185° C.

2.7 g of the compound 26 and 2.5 ml of methyl iodide were placed in 27 ml of DMA and cooled to −10° C. 0.45 g of NaH, 60% dispersion in mineral oil, was added and stirred for 30 min. at −5° C. Then 10 g of ice and 5 ml of 2N HCl were added and the mixture was concentrated by evaporation. The residue was extracted with ethyl acetate and water, the organic phase was dried, evaporated to dryness and filtered through silica gel.

Yield: 3.0 g of compound 27 (oil).

$^1$H-NMR (250 MHz): =7.67 (1H, s), 4.32–4.07 (m, 2H), 3.32 (s, 3H), 3.08 (m, 1H), 1.70–1.50 (m, 3H), 1.42 (d, 3H), 0.95 (m, 6H).

SYNTHESIS OF EXAMPLE 171

0.28 g of compound 27, 0.9 mL of sulpholane and 0.22 g of p-aminobenzoic acid-benzylamide were stirred for 0.5 h at 170° C., then the mixture was combined with ether and the crystals were filtered off. The product was recrystallised from ethanol.

Yield: 0,15 g, melting point: 228–240° C. (yellowish crystals).

The compounds of formula (I) listed in Table 1 are obtained analogously to the process described above.

The abbreviations $X_2$, $X_3$, $X_4$, $X_5$ and $X_6$ used in Table 1 in each case denote a link to a position in the general formula shown under Table 1 instead of the corresponding groups $R^2$, $R^3$, $R^4$, $R^5$ and $R^6$.

TABLE 1

| Ex. | $R^2$ | $R^3$ | $R^4$ | config. $R^3$ or $R^4$ | $R^5$ | $R^6$ | mp. [° C.] |
|---|---|---|---|---|---|---|---|
| 1 | $X_2$–$CH_3$ | H | H | rac. | $CH_3$–$X_5$ | 9-ethyl-carbazol-3-yl ($X_6$) | |
| 2 | $CH_3$, $X_2$ | $X_3$–$CH_3$ | H | rac. | $X_5$–CH($CH_3$)$_2$ (isobutyl) | N-(pyridin-3-ylmethyl)-4-($X_6$)benzamide | 208 |

TABLE 1-continued

| Ex. | R² | R³ | R⁴ | config. R³ or R⁴ | R⁵ | R⁶ | mp. [° C.] |
|---|---|---|---|---|---|---|---|
| 3 | CH₃, X₂ | X₃–CH₃ | H | rac. | X₅–CH₂–CH₂–CH(CH₃)CH₃ | N-(pyridin-3-yl)-4-X₆-benzamide | 241 |
| 4 | X₂, CH₃ | H₃C–X₃ | H | rac. | X₅–CH₂–C(CH₃)₂–CH₃ (neopentyl) | 4-X₆-N-(pyridin-3-yl)benzamide | — |
| 5 | CH₃, X₂ | X₃–CH₂–CH₃ | H | rac. | X₅–CH₂–CH₂–CH(CH₃)CH₃ | 4-X₆-N-(pyridin-3-ylmethyl)benzamide | 175 |
| 6 | X₂, CH₃ | H₃C–X₃ | H | rac. | H₃C–CH(CH₃)–CH₂–CH₂–X₅ | 4-X₆-N-(pyridin-3-ylmethyl)benzamide | 190 |
| 7 | X₂, CH₃ | H₃C–(CH₂)₂–X₃ | H | rac. | cyclopropylmethyl-X₅ | 4-X₆-N-(pyridin-3-yl)benzamide | — |

TABLE 1-continued

| Ex. | R² | R³ | R⁴ | config. R³ or R⁴ | R⁵ | R⁶ | mp. [° C.] |
|---|---|---|---|---|---|---|---|
| 8 | CH₃ (X₂) | X₃—CH₃ | H | rac. | X₅—CH₂CH₂-cyclopropyl | X₆—C₆H₄—C(O)NH—CH₂-(3-pyridyl) | 200 |
| 9 | CH₃ (X₂) | X₃—CH₂CH₃ | H | rac. | X₅—CH₂CH(CH₃)₂ (isobutyl, shown as X₅—CH₂—CH(CH₃)—CH₃ = 3-methylbutyl) | X₆—C₆H₄—C(O)NH—CH₂CH₂-(3-pyridyl) | 168 |
| 10 | CH₃ (X₂) | X₃—CH₃ | H | rac. | X₅—CH₂CH₂—C(CH₃)₃ | X₆—C₆H₄—C(O)NH—CH₂-(3-pyridyl) | 190 |
| 11 | CH₃ (X₂) | X₃—CH₃ | H | rac. | X₅—CH₂—CH(CH₃)—CH₃ (isobutyl, with additional CH₃) | (3-pyridyl)—NH—C(O)—C₆H₄—X₆ | — |

TABLE 1-continued

| Ex. | R² | R³ | R⁴ | config. R³ or R⁴ | R⁵ | R⁶ | mp. [° C.] |
|---|---|---|---|---|---|---|---|
| 12 | X₂, CH₃ | X₃–CH₃ | H | rac. | CH₃–CH₂–CH₂–CH(X₅)– (butyl with X₅) | 4-X₆-C₆H₄-C(O)-NH-CH₂-(3-pyridyl) | |
| 13 | CH₃, X₂ | X₃–CH₃ | H | rac. | X₅-CH₂-CH(CH₃)-CH₃ (isobutyl) | 4-X₆-C₆H₄-C(O)-NH-CH₂-(3-pyridyl) | 145 |
| 14 | CH₃, X₂ | X₃–CH₂–CH₃ | H | rac. | X₅-CH₂-CH(CH₃)-CH₃ (isobutyl) | 4-X₆-C₆H₄-C(O)-NH-CH₂-(3-pyridyl) | |
| 15 | X₂, CH₃ | H₃C–CH₂–X₃ | H | rac. | cyclopropyl-CH₂-X₅ | 4-X₆-C₆H₄-C(O)-NH-CH₂-(3-pyridyl) | 55 |

TABLE 1-continued

| Ex. | R² | R³ | R⁴ | config. R³ or R⁴ | R⁵ | R⁶ | mp. [° C.] |
|---|---|---|---|---|---|---|---|
| 16 | CH₃ (X₂) | X₃—CH₃ (ethyl) | H | rac. | X₅—CH₂CH₂CH(CH₃)₂ (isopentyl) | X₆—C₆H₄—C(O)NH—(pyridin-3-yl) | 250 |
| 17 | CH₃ (X₂) | X₃—CH₃ (ethyl) | H | rac. | X₅—CH₂CH₂CH(CH₃)₂ (isopentyl) | X₆—(3-methoxyphenyl)—C(O)NH—CH₂—(pyridin-4-yl) | 204 |
| 18 | CH₃ (X₂) | X₃—CH₃ | H | rac. | X₅—CH₂-cyclopropyl | X₆—C₆H₄—C(O)NH—CH₂—(pyridin-3-yl) | |
| 19 | X₂—CH₃ | H₃C—X₃ | H | rac. | X₅—CH₂C(CH₃)₃ (neopentyl) | X₆—C₆H₄—C(O)NH—CH₂—(pyridin-3-yl) | |

TABLE 1-continued

| Ex. | R² | R³ | R⁴ | config. R³ or R⁴ | R⁵ | R⁶ | mp. [° C.] |
|---|---|---|---|---|---|---|---|
| 20 | X₂–CH₃ | H₃C–X₃ | H | R | (CH₃)₂CHCH₂CH₂–X₅ (isopentyl) | X₆–C₆H₄–C(O)NH–(pyridin-3-yl) | 221 |
| 21 | CH₃, X₂ | X₃–CH₂CH₃ | H | rac. | X₅–CH₂CH₂CH(CH₃)₂ | 3-methoxy-4-X₆-C₆H₃–C(O)NH–CH₂–(pyridin-3-yl) | 172 |
| 22 | CH₃, X₂ | X₃–CH₂CH₃ | H | rac. | X₅–CH₂CH₂CH(CH₃)₂ | X₆–C₆H₄–C(O)NH–CH₂–(pyridin-4-yl) | 221 |
| 23 | CH₃, X₂ | X₃–CH₂CH₃ | H | rac. | X₅–CH₂–cyclopropyl | (pyridin-3-yl)–CH₂–NH–C(O)–C₆H₄–X₆ | — |
| 24 | X₂–CH₃ | H₃C–X₃ | H | rac. | (CH₃)₃C–CH₂–X₅ (neopentyl) | X₆–C₆H₄–C(O)NH–CH₂–C₆H₄–OH | 210 |

TABLE 1-continued

| Ex. | R² | R³ | R⁴ | config. R³ or R⁴ | R⁵ | R⁶ | mp. [° C.] |
|---|---|---|---|---|---|---|---|
| 25 | X₂, CH₃ | H₃C–X₃ | H | R | H₃C, CH₃ (isopentyl-X₅) | 3-methoxy-4-X₆-benzoyl-N-(pyridin-4-ylmethyl) | 213 |
| 26 | CH₃, X₂ | X₃–CH₂CH₃ | H | rac. | X₅-isopentyl (H₃C, CH₃) | 4-X₆-3-methoxy-benzoyl-N-(3-(imidazol-1-yl)propyl) | 188 |
| 27 | X₂, CH₃ | X₃–CH₂CH₃ | H | rac. | cyclopropylmethyl-X₅ | 2-chloro-4,6-dimethyl-3-(N-(4-X₆-benzoyl)aminomethyl)pyridine | — |
| 28 | X₂, CH₃ | X₃–CH₃ | H | S | H₃C, CH₃ (isopentyl-X₅) | N-(pyridin-3-ylmethyl)-4-X₆-benzoyl | — |
| 29 | CH₃, X₂ | X₃–CH₂CH₃ | H | rac. | X₅-isopentyl (H₃C, CH₃) | 4-X₆-3-methyl-N-(pyridin-4-ylmethyl)benzoyl | 178 |

TABLE 1-continued

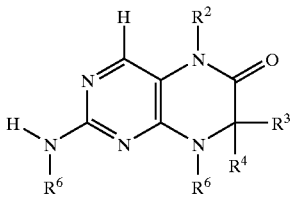

| Ex. | R² | R³ | R⁴ | config. R³ or R⁴ | R⁵ | R⁶ | mp. [° C.] |
|---|---|---|---|---|---|---|---|
| 30 | X₂—CH₃ | X₃—CH₃ | H | R | H₃C—CH(CH₃)—CH₂—CH₂—X₅ | 4-X₅-C₆H₄-C(O)-NH-CH₂-(4-pyridyl) | 175 |
| 31 | X₂—CH₃ | X₃—CH₃ | H | rac. | X₅-CH₂-CH₂-CH(CH₃)-CH₃ | 4-X₆-C₆H₄-C(O)-NH-CH₂CH₂-(3-pyridyl) | — |
| 32 | CH₃—X₂ | X₃—CH₃ | H | rac. | X₅-CH₂-CH(CH₃)-CH₃ (H₃C) | 4-X₆-C₆H₄-C(O)-NH-CH₂-(4-pyridyl) | 221 |
| 33 | X₂—CH₃ | X₃—CH₃ | H | R | H₃C—CH(CH₃)—CH₂—CH₂—X₅ | 4-X₆-3-OCH₃-C₆H₃-C(O)-NH-CH₂-(3-pyridyl) | 124 |
| 34 | X₂—CH₃ | H₃C—X₃ | H | rac. | H₃C-C(CH₃)₂-CH₂-X₅ | 4-X₆-C₆H₄-C(O)-NH-CH₂-C₆H₅ | 136 |
| 35 | CH₃—X₂ | X₃—CH₃ (ethyl) | H | rac. | X₅-CH₂-CH₂-CH(CH₃)-CH₃ | 2-(pyrazin-2-yl)-benzimidazol-1-yl | 162 |

TABLE 1-continued
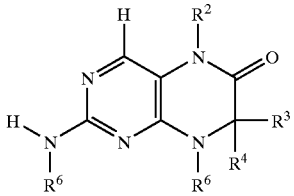
| Ex. | R² | R³ | R⁴ | config. R³ or R⁴ | R⁵ | R⁶ | mp. [° C.] |
|---|---|---|---|---|---|---|---|
| 36 | CH₃ X₂ | X₃—CH₃ | H | rac. | X₅—CH₂CH(CH₃)CH₃ | 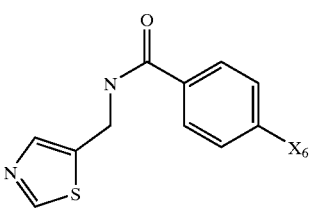 | 169 |
| 37 | CH₃ X₂ | X₃—CH₃ | H | rac. | X₅—CH₂CH₂C(CH₃)₂CH₃ | 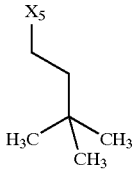 | 219 |
| 38 | CH₃ X₂ | X₃—CH₂CH₃ | H | rac. | X₅—CH₂CH(CH₃)CH₃ |  | 179 |
| 39 | CH₃ X₂ | X₃—CH₂CH₃ | H | rac. | X₅—CH₂CH(CH₃)CH₃ |  | 211 |

TABLE 1-continued
| Ex. | R² | R³ | R⁴ | config. R³ or R⁴ | R⁵ | R⁶ | mp. [° C.] |
|---|---|---|---|---|---|---|---|
| 40 | CH₃, X₂ | X₃—CH₃ | H | rac. |  | 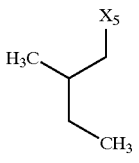 | |
| 41 | X₂, CH₃ | H₃C—X₃ | H | rac. | 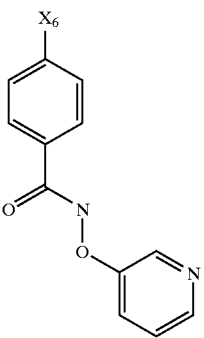 |  | |
| 42 | X₂, CH₃ | H₃C—X₃ | H | R |  | 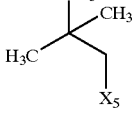 | 100 |
| 43 | X₂, CH₃ | H₃C—X₃ | H | rac. | 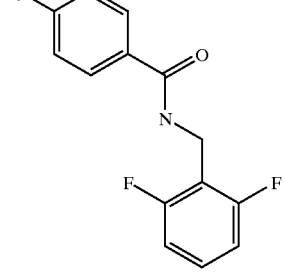 |  | 175 |

TABLE 1-continued

[Structure: 2-amino-pteridinone core with substituents R2, R3, R4, R5, R6]

| Ex. | R² | R³ | R⁴ | config. R³ or R⁴ | R⁵ | R⁶ | mp. [° C.] |
|---|---|---|---|---|---|---|---|
| 44 | CH₃–X₂ | X₃–CH₂–CH₃ | H | rac. | X₅–CH₂–CH₂–CH(CH₃)₂ | 4-X₆-3-methoxy-benzamide | 203 |
| 45 | CH₃–X₂ | X₃–CH₂–CH₃ | H | rac. | X₅–CH₂–cyclopropyl | N-(thiazol-5-ylmethyl)-4-X₅-benzamide | 165 |
| 46 | CH₃–X₂ | X₃–CH₂–CH₃ | H | rac. | X₅–CH₂–CH₂–CH(CH₃)₂ | 4-X₆-3-methoxy-N-(pyridin-2-ylmethyl)benzamide | |
| 47 | X₂–CH₃ | X₃–CH₂–CH₃ | H | rac. | X₅–CH₂–cyclopropyl | N-[(6-chloro-2-methylpyridin-3-yl)methyl]-4-X₆-benzamide | |
| 48 | X₂–CH₃ | H₃C–X₃ | H | rac. | X₅–CH₂–C(CH₃)₃ | 4-X₆-N-[(6-methylpyridin-3-yl)methyl]benzamide | |

TABLE 1-continued

| Ex. | R² | R³ | R⁴ | config. R³ or R⁴ | R⁵ | R⁶ | mp. [° C.] |
|---|---|---|---|---|---|---|---|
| 49 | X₂—CH₃ (CH₃) | H₃C—X₃ | H | rac. | neopentyl-X₅ (C(CH₃)₃CH₂) | X₆-C₆H₃-C(O)-NH-CH₂-C₆H₂(F)₂-OH | |
| 50 | CH₃, X₂ | X₃—CH₂CH₃ | H | rac. | X₅-CH₂CH₂-CH(CH₃)₂ | X₆-C₆H₄-C(O)-NH₂ | 212 |
| 51 | X₂—CH₃ | X₃—CH₃ | H | S | (CH₃)₂CH-CH₂CH₂-X₅ | pyridin-3-yl-NH-C(O)-C₆H₄-X₆ | |
| 52 | CH₃, X₂ | X₃—CH₃ | H | rac. | X₅-CH₂-CH(CH₃)₂ CH₃ | HO-C₆H₄-CH₂-NH-C(O)-C₆H₄-X₆ | |
| 53 | X₂—CH₃ | H₃C—X₃ | H | rac. | neopentyl-X₅ | X₆-C₆H₄-C(O)-NH-CH₂-(thiophen-2-yl) | |

TABLE 1-continued
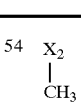
| Ex. | R² | R³ | R⁴ | config. R³ or R⁴ | R⁵ | R⁶ | mp. [° C.] |
|---|---|---|---|---|---|---|---|
| 54 | 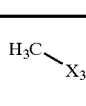 | 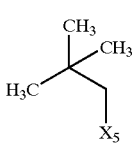 | H | rac. | 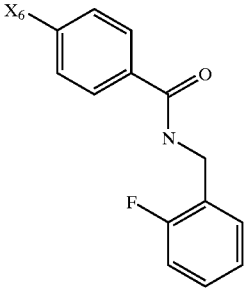 |  |  |
| 55 | 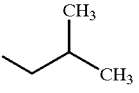 | 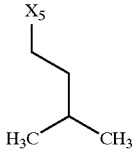 | H | rac. | 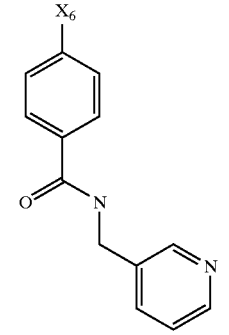 |  | 191 |
| 56 | 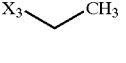 | 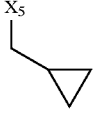 | H | rac. | 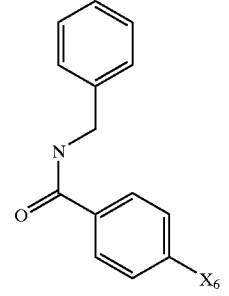 |  | 158 |
| 57 |  | 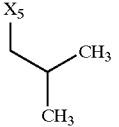 | H | rac. | 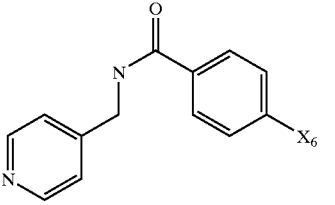 | (see above) | 230 |

TABLE 1-continued

| Ex. | R² | R³ | R⁴ | config. R³ or R⁴ | R⁵ | R⁶ | mp. [° C.] |
|---|---|---|---|---|---|---|---|
| 58 | X₂—CH₃ | H₃C—X₃ | H | rac. | (CH₃)₃C—CH₂—X₅ (neopentyl) | X₈—C₆H₄—C(O)—NH—CH₂-(pyridin-4-yl) | |
| 59 | X₂—CH₃ | H₃C—X₃ | H | R | (CH₃)₂CH—CH₂—CH₂—X₅ (isopentyl) | X₆-(3-methoxy-phenyl)—C(O)—NH-(pyridin-4-yl) | 125 |
| 60 | X₂—CH₃ | H | H | rac. | (CH₃)₂CH—CH₂—X₅ (isobutyl) | (pyridin-3-yl)—CH₂—NH—C(O)—C₆H₄—X₆ | 250 |
| 61 | X₂—CH₃ | X₃—CH₂—CH₃ | H | rac. | X₅—CH₂—CH(CH₃)—CH₃ (isobutyl) | X₆—C₆H₄—C(O)—NH—CH₂-(pyridin-4-yl) | |

TABLE 1-continued
| Ex. | R² | R³ | R⁴ | config. R³ or R⁴ | R⁵ | R⁶ | mp. [° C.] |
|---|---|---|---|---|---|---|---|
| 62 | CH₃ X₂ | X₃—CH₃ (ethyl) | H | rac. |  | 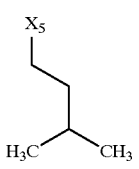 | 169 |
| 63 | CH₃ X₂ | X₃—CH₃ (ethyl) | H | rac. | 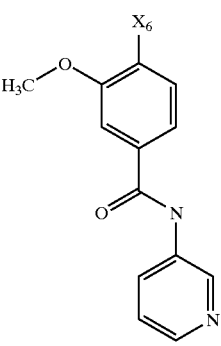 |  | 178 |
| 64 | CH₃ X₂ | X₃—CH₃ | H | rac. |  | 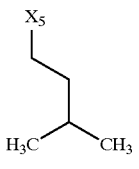 | |
| 65 | CH₃ X₂ | X₃—CH₃ | H | rac. | 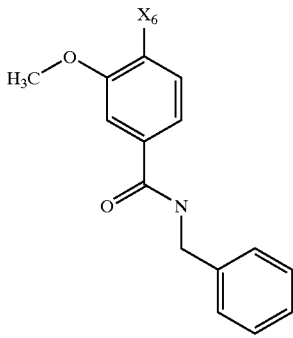 |  | |

TABLE 1-continued

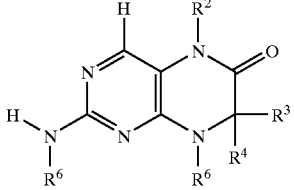

| Ex. | R² | R³ | R⁴ | config. R³ or R⁴ | R⁵ | R⁶ | mp. [° C.] |
|---|---|---|---|---|---|---|---|
| 66 | X₂—CH₃ | X₃—CH₃ | H | R | H₃C—CH(CH₃)—CH₂—CH₂—X₅ (isopentyl with X₅) | X₆—C₆H₄—C(O)—NH—(4-pyridyl) | 225 |
| 67 | CH₃, X₂ | X₃—CH₃ | H | rac. | H₃C—CH(CH₃)—CH(CH₃)—CH₂—X₅ | X₆—C₆H₄—C(O)—NH—CH₂—(4-pyridyl) | |
| 68 | X₂, CH₃ | H₃C—X₃ | H | rac. | (CH₃)₃C—CH₂—X₅ (neopentyl) | X₆—C₆H₄—C(O)—NH—CH₂—(2-methyl-6-chloro-3-pyridyl) | |
| 69 | CH₃, X₂ | X₃—CH₃ | H | rac. | X₅—CH₂—CH(CH₃)—CH₃ (isobutyl) | HO—C₆H₄—CH₂—NH—C(O)—C₆H₄—X₆ | |
| 70 | CH₃, X₂ | X₃—CH₃ | H | rac. | cyclopropyl—CH₂—X₅ | X₆—C₆H₄—C(O)—NH—(CH₂)₃—(1-imidazolyl) | |

TABLE 1-continued

| Ex. | R² | R³ | R⁴ | config. R³ or R⁴ | R⁵ | R⁶ | mp. [° C.] |
|---|---|---|---|---|---|---|---|
| 71 | X₂—CH₃ | H₃C—X₃ | H | rac. | neopentyl (X₅—C(CH₃)₃) | 4-(X₆)-C₆H₄-C(O)-NH-CH₂-(thiazol-5-yl) | |
| 72 | X₂—CH₃ | X₃—CH₂CH₃ | H | rac. | isobutyl (X₅—CH₂CH(CH₃)₂) | 4-(X₆)-C₆H₄-C(O)-NH-CH₂-C₆H₅ | |
| 73 | X₂—CH₃ | X₃—CH₂CH₃ | H | rac. | isopentyl (X₅—CH₂CH₂CH(CH₃)₂) | 3-HO-4-(X₆)-C₆H₃-C(O)-NH-CH₂-(pyridin-4-yl) | |
| 74 | X₂—CH₃ | azetidine (X₃–X₄) | | | isopentyl (X₅—CH₂CH₂CH(CH₃)₂) | 3-CH₃O-4-(X₆)-C₆H₃-C(O)-NH-CH₂-(pyridin-3-yl) | 167 |

TABLE 1-continued
| Ex. | R² | R³ | R⁴ | config. R³ or R⁴ | R⁵ | R⁶ | mp. [° C.] |
|---|---|---|---|---|---|---|---|
| 75 | X₂—CH(CH₃) | H₃C—X₃ | H | rac. |  | 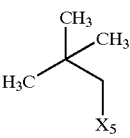 | |
| 76 | CH(CH₃)—X₂ | X₃—CH₃ | H | rac. | 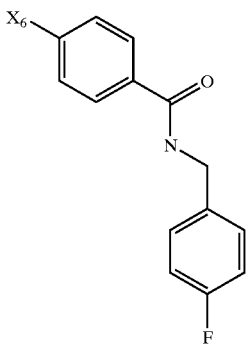 |  | 246 |
| 77 | X₂—CH(CH₃) | H₃C—X₃ | H | rac. |  | 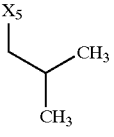 | |
| 78 | CH(CH₃)—X₂ | X₃—CH₃ | H | rac. | 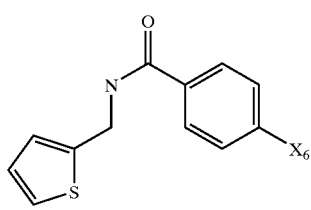 |  | 172 |

TABLE 1-continued

| Ex. | R² | R³ | R⁴ | config. R³ or R⁴ | R⁵ | R⁶ | mp. [° C.] |
|-----|----|----|----|------------------|----|----|------------|
| 79 | CH₃, X₂ | X₃–CH₂–CH₃ | H | rac. | X₅–CH(CH₃)–CH(CH₃)₂ | X₆–C₆H₄–C(O)NH–CH₂–(3-pyridyl) | 170 |
| 80 | CH₃, X₂ | X₃–CH₃ | X₄–CH₃ | rac. | X₅–CH₂–CH₂–CH(CH₃)₂ | 4-carbamoyl-2-methoxyphenyl (X₆ at 4-position, H₂NC(O), OCH₃) | 222 |
| 81 | CH₃, X₂ | X₃–CH₃ | H | rac. | X₅–CH₂–CH₂–CH(CH₃)₂ | 6-methylpyridin-3-yl-CH₂–NHC(O)–C₆H₄–X₆ | 187 |
| 82 | CH₃, X₂ | X₃–CH₃ | H | rac. | X₅–CH₂–CH₂–CH(CH₃)₂ | thien-2-yl–CH₂–NHC(O)–C₆H₄–X₆ | 215 |
| 83 | CH₃, X₂ | X₃–X₄ cyclopropyl | | rac. | X₅–CH₂–CH₂–CH(CH₃)₂ | 3-methoxy-4-X₆-phenyl–C(O)NH–(3-pyridyl) | 199 |

TABLE 1-continued

| Ex. | R² | R³ | R⁴ | config. R³ or R⁴ | R⁵ | R⁶ | mp. [° C.] |
|---|---|---|---|---|---|---|---|
| 84 | CH₃, X₂ | X₃—CH₃ | X₄—CH₃ | rac. | X₅—CH₂CH₂CH(CH₃)₂ (isopentyl) | N-methoxy-N-methyl 3-methoxy-4-X₆-benzamide | 127 |
| 85 | X₂, CH₃ | H₃C—X₃ | H | rac. | neopentyl (X₅—CH₂C(CH₃)₃) | 4-X₆-N-(6-chloropyridin-3-yl)benzamide | — |
| 86 | CH₃, X₂ | X₃—CH₃ | H | rac. | isobutyl (X₅—CH₂CH(CH₃)₂) | N-allyl-4-X₆-benzamide | 169 |
| 87 | CH₃, X₂ | X₃—CH₃ | H | rac. | isobutyl (X₅—CH₂CH(CH₃)₂) | N-benzyl-4-X₆-benzamide | 250 |
| 88 | CH₃, X₂ | X₃—CH₃ | H | rac. | X₅—CH₂CH₂C(CH₃)₃ | 3-methoxy-4-X₆-N-(3,4,5-trimethoxyphenyl)benzamide | 233 |

TABLE 1-continued

[Structure: pteridinone core scaffold with substituents R², R³, R⁴, R⁵, R⁶ as shown]

| Ex. | R² | R³ | R⁴ | config. R³ or R⁴ | R⁵ | R⁶ | mp. [° C.] |
|---|---|---|---|---|---|---|---|
| 89 | CH₃ (X₂) | X₃–CH₂–CH₃ | H | rac. | X₅–CH₂–CH(CH₃)–CH₃ (isopentyl) | X₆–(5-benzimidazolyl)-2-phenyl-benzimidazole | 160 |
| 90 | CH₃ (X₂) | X₃–CH₃ | H | rac. | X₅–CH₂–CH(CH₃)₂ (isobutyl) | N-(2-pyridylmethyl)-4-(X₆)-benzamide | 154 |
| 91 | X₂, CH₃ | H₃C–CH(X₃)– | H | rac. | cyclopropylmethyl (X₅) | 3-methoxy-4-(X₆)-N-(3-pyridylmethyl)benzamide | |
| 92 | CH₃ (X₂) | X₃–CH₂–CH₃ | H | rac. | X₅–CH₂–CH(CH₃)–CH₃ | 4-(X₆)-N-(2-pyridylmethyl)benzamide | |

TABLE 1-continued

| Ex. | R² | R³ | R⁴ | config. R³ or R⁴ | R⁵ | R⁶ | mp. [° C.] |
|---|---|---|---|---|---|---|---|
| 93 | X₂—CH₃ | H₃C—X₃ | H | rac. | (CH₃)₃C-CH₂-X₅ (neopentyl) | X₆-C₆H₄-C(O)-NH-CH₂-(3-F-C₆H₄) | |
| 94 | X₂—CH₃ | H₃C—X₃ | H | R | (CH₃)₂CH-CH₂-CH₂-X₅ (isoamyl) | 4-X₆-3-OCH₃-C₆H₃-C(O)-NH-CH₂-C₆H₅ | |
| 95 | CH₃, X₂ | X₃—CH₂—CH₃ | H | rac. | X₅-CH₂-CH(CH₃)-CH₃ | X₆-C₆H₄-C(O)-NH-CH₂-(3-NH₂-C₆H₄) | 150 |
| 96 | CH₃, X₂ | X₃—CH₂—CH₃ | X₄—CH₂—CH₃ | rac. | X₅-CH₂-CH₂-CH(CH₃)-CH₃ | X₆-C₆H₄-C(O)-NH₂ | 300 |

TABLE 1-continued
| Ex. | R² | R³ | R⁴ | config. R³ or R⁴ | R⁵ | R⁶ | mp. [° C.] |
|---|---|---|---|---|---|---|---|
| 97 | X₂—CH₃ | H₃C—X₃ | H | rac. | neopentyl (X₅CH₂C(CH₃)₃) |  | 243 |
| 98 | CH₃, X₂ | X₃—CH₃ | H | rac. | isopentyl (X₅CH₂CH₂CH(CH₃)₂) | 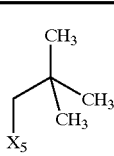 | 209 |
| 99 | CH₃, X₂ | X₃—CH₂—CH₃ | H | rac. | isopentyl (X₅CH₂CH₂CH(CH₃)₂) | 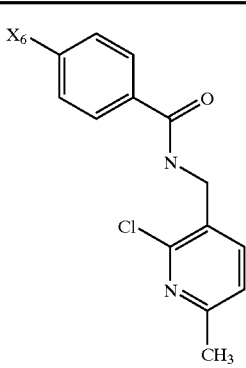 | 182 |
| 100 | X₂, CH₃ | X₃—CH₃ | H | rac. | n-pentyl (X₅(CH₂)₄CH₃) |  | |

TABLE 1-continued

| Ex. | R² | R³ | R⁴ | config. R³ or R⁴ | R⁵ | R⁶ | mp. [° C.] |
|---|---|---|---|---|---|---|---|
| 101 | X₂, CH₃ | X₃—CH₃ | H | R | H₃C-CH(CH₃)-CH₂-CH₂-X₅ (isopentyl with X₅) | X₆-C₆H₄-C(O)-N(H)-phenyl | 232 |
| 102 | CH₃, X₂ | X₃—CH₃ | H | rac. | X₅-CH₂-CH(CH₃)-CH₂-CH₃ | X₆-C₆H₄-C(O)-NH-CH₂-(2-pyridyl) | |
| 103 | CH₃, X₂ | X₃—CH₃ | H | rac. | X₅-CH₂-CH(CH₃)-CH₃ (isobutyl) | 3,5-difluoro-4-hydroxybenzyl-NH-C(O)-C₆H₄-X₆ | |
| 104 | CH₃, X₂ | X₃—CH₂—CH₃ | H | rac. | X₅-CH₂-CH(CH₃)-CH₃ (isopentyl, H₃C-CH-CH₃) | 3-methoxy-4-X₆-C₆H₃-C(O)-NH-(4-pyridyl) | 146 |

TABLE 1-continued

| Ex. | R² | R³ | R⁴ | config. R³ or R⁴ | R⁵ | R⁶ | mp. [° C.] |
|---|---|---|---|---|---|---|---|
| 105 | CH₃, X₂ | X₃—CH₃ | H | rac. | X₅—CH₂CH₂—CH(CH₃)₂ | 6-methoxypyridin-3-yl-NH-C(O)-C₆H₄-X₆ (para) | 209 |
| 106 | CH₃, X₂ | X₃—CH₃ | H | rac. | X₅—CH₂CH₂—C(CH₃)₃ | 3-methoxy-4-X₆-phenyl-C(O)NH₂ | 286 |
| 107 | X₂—CH₃ | X₃—CH₃ | H | rac. | X₅—CH₂CH₂CH₂—CH₃ | pyridin-2-yl-CH₂—NH—C(O)—C₆H₄—X₆ (para) | — |
| 108 | X₂—CH₃ | X₃—CH₃ | H | R | X₅—CH₂CH₂—CH(CH₃)₂ | 3-methoxy-4-X₆-phenyl-C(O)—NH-phenyl | 202 |

TABLE 1-continued

| Ex. | R² | R³ | R⁴ | config. R³ or R⁴ | R⁵ | R⁶ | mp. [° C.] |
|---|---|---|---|---|---|---|---|
| 109 | CH₃, X₂ | X₃–CH₃ (ethyl) | H | rac. | X₅–CH₂–CH(CH₃)–CH₃ (isobutyl on CH₂) - 3-methylbutyl | X₆-benzimidazole-2-(4-pyridyl) | 180 |
| 110 | CH₃, X₂ | X₃–CH₃ | H | rac. | X₅–CH₂–CH(CH₃)₂ (isobutyl) | cyclohexyl-CH₂–NH–C(=O)–C₆H₄–X₆ | — |
| 111 | X₂, CH₃ | H₃C–CH₂–CH₂–X₃ | H | rac. | cyclopropyl-CH₂–X₅ | X₆–C₆H₃(OCH₃)–C(=O)–NH–CH₂–(4-pyridyl) | 250 |
| 112 | CH₃, X₂ | X₃–CH₃ | H | rac. | X₅–CH₂–C(CH₃)₃ (neopentyl) | X₆–C₆H₄–C(=O)–NH–CH₂–(2-pyridyl) | — |

TABLE 1-continued
| Ex. | R² | R³ | R⁴ | config. R³ or R⁴ | R⁵ | R⁶ | mp. [° C.] |
|---|---|---|---|---|---|---|---|
| 113 | X₂—CH₃, CH₃ | X₃—CH₃ | H | rac. |  | 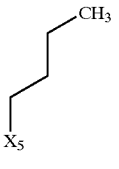 | |
| 114 | CH₃, X₂ | X₃—CH₃ | X₄—CH₃ | | 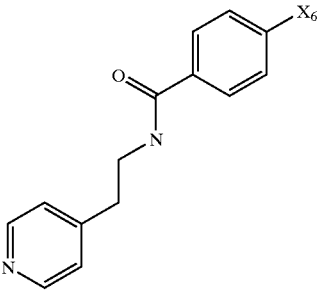 |  | 237 |
| 115 | CH₃, X₂ | X₃—CH₃ | H | rac. |  |  | 135 |
| 116 | X₂, CH₃ | H₃C—X₃ | H | rac. | 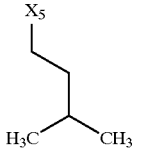 | 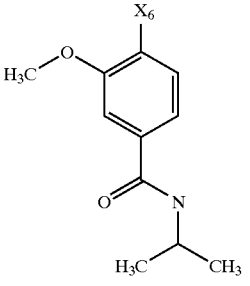 | |

TABLE 1-continued
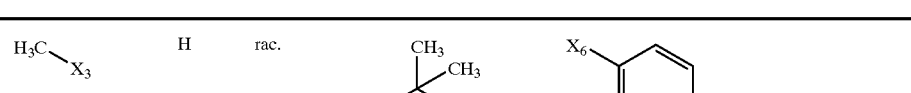
| Ex. | R² | R³ | R⁴ | config. R³ or R⁴ | R⁵ | R⁶ | mp. [° C.] |
|---|---|---|---|---|---|---|---|
| 117 | X₂—CH₃ | H₃C—X₃ | H | rac. | (CH₃)₃C-CH₂-X₅ (neopentyl) | X₆-C₆H₄-C(O)-NH-CH₂-(2-OCHF₂-C₆H₄) | |
| 118 | CH₃-X₂ | X₃—CH₂—CH₃ | H | rac. | X₅-CH₂-CH(CH₃)₂ | X₆-C₆H₄-C(O)-NH-CH₂-(3-F-C₆H₄) | |
| 119 | CH₃-X₂ | X₃—CH₂—CH₃ | H | rac. | X₅-CH₂-CH(CH₃)₂ | X₆-benzimidazol-2-yl(3-pyridyl) | 213 |
| 120 | CH₃-X₂ | X₃—CH₂—CH₃ | H | rac. | X₅-CH₂-CH₂-CH(CH₃)₂ | X₆-(3-methyl-2-phenyl-3H-indol-6-yl) | 198 |

TABLE 1-continued

| Ex. | R² | R³ | R⁴ | config. R³ or R⁴ | R⁵ | R⁶ | mp. [° C.] |
|---|---|---|---|---|---|---|---|
| 121 | CH₃, X₂ | X₃—CH₃ (ethyl) | H | rac. | X₅—CH₂CH(CH₃)₂ (isopentyl) | X₆-5-(1-methyl-2-(pyridin-2-ylmethyl)benzimidazolyl) | |
| 122 | CH₃, X₂ | X₃—CH₃ (ethyl) | H | rac. | X₅—CH₂CH(CH₃)₂ (isopentyl) | X₆-4-(3-methyl)-N-(pyridin-2-ylmethyl)benzamide | |
| 123 | X₂, CH₃ | H₃C—X₃ | H | rac. | H₃C-C(CH₃)₂-CH₂-X₅ (neopentyl) | X₆-4-N-(2-methoxybenzyl)benzamide | |
| 124 | X₂, CH₃ | X₃—CH₂CH₃ | H | rac. | cyclopropylmethyl-X₅ | H₃C-6-methyl-2-chloro-pyridin-3-yl-CH₂-N(H)-C(O)-C₆H₄-X₆ | |
| 125 | CH₃, X₂ | X₃—CH₃ (ethyl) | H | rac. | X₅—CH₂CH(CH₃)CH₃ (isobutyl) | 2-(4-X₆-phenyl)benzimidazol-1-yl | 287 |

TABLE 1-continued
| Ex. | R² | R³ | R⁴ | config. R³ or R⁴ | R⁵ | R⁶ | mp. [° C.] |
|---|---|---|---|---|---|---|---|
| 126 | CH₃–X₂ | X₃–CH₂–CH₃ | H | rac. | X₅–CH₂–CH₂–CH(CH₃)₂ | X₆-(5-position of 1-methyl-2-(pyrazin-2-yl)benzimidazole) | 195 |
| 127 | CH₃–X₂ | X₃–CH₃ | H | rac. | X₅–CH₂–CH(CH₃)₂ | X₆-(3-position of N-benzylbenzamide) | |
| 128 | X₂–CH₃ (on CH) | H₃C–X₃ | H | rac. | H₃C–C(CH₃)₂–CH₂–X₅ | X₆-(4-position of N-(3-methoxybenzyl)benzamide) | |
| 129 | CH₃–X₂ | X₃–CH₃ | H | rac. | X₅–CH₂–CH₂–C(CH₃)₃ | X₆-(4-position of N-benzylbenzamide) | 247 |

TABLE 1-continued

| Ex. | R² | R³ | R⁴ | config. R³ or R⁴ | R⁵ | R⁶ | mp. [° C.] |
|---|---|---|---|---|---|---|---|
| 130 | X₂—CH₃ | X₃—CH₃ | H | rac. | X₅—CH₂CH(CH₃)₂ | X₆-(3-benzamido)-CH₂-(5-methylpyrazin-2-yl) | |
| 131 | X₂—CH₃ | X₃—CH₃ | X₄—CH₃ | | X₅—CH₂CH₂CH(CH₃)₂ | X₆-(4-benzamido)-N-(pyridin-3-yl) | 281 |
| 132 | X₂—CH₃ | X₃—CH₃ | H | rac. | X₅—CH(CH₃)CH₂CH₃ with X₃ branch | X₆-(4-benzamide) | |
| 133 | X₂—CH₃ | X₃—CH₃ | H | rac. | X₅—CH₂CH(CH₃)₂ | X₆-(4-benzamide) | |

TABLE 1-continued

| Ex. | R² | R³ | R⁴ | config. R³ or R⁴ | R⁵ | R⁶ | mp. [° C.] |
|---|---|---|---|---|---|---|---|
| 134 | CH₃, X₂ | X₃—CH₃ | H | rac. | X₅—cyclopropylmethyl | X₆—C₆H₄—C(O)NH—CH₂—C₆H₅ | 208 |
| 135 | X₂, CH₃ | X₃—CH₃ | H | rac. | X₅—CH₂CH₂CH(CH₃) butyl | X₆—C₆H₄—C(O)NH—CH₂CH₂—(2-pyridyl) | |
| 136 | X₂, CH₃ | X₃—CH₃ | H | R | X₅—CH₂CH₂CH(CH₃)₂ | X₆—C₆H₄—C(O)NH—CH₂—C₆H₅ | 192 |
| 137 | X₂, CH₃ | X₃—CH₃ | H | rac. | X₅—CH₂CH₂CH(CH₃) butyl | 4-(CH₃OC(O))—C₆H₄—CH₂—NH—C(O)—C₆H₄—X₆ | 212 |
| 138 | X₂, CH₃ | H₃C—X₃ | H | rac. | X₅—CH₂—C(CH₃)₃ neopentyl | X₆—C₆H₄—C(O)NH—CH₂—C₆H₄—O—CHF₂ | |

TABLE 1-continued
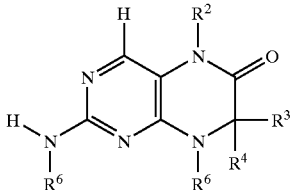
| Ex. | R² | R³ | R⁴ | config. R³ or R⁴ | R⁵ | R⁶ | mp. [° C.] |
|---|---|---|---|---|---|---|---|
| 139 | CH₃ X₂ | X₃―CH₃ (ethyl) | H | rac. | X₅―CH(CH₃)₂ (isobutyl) | 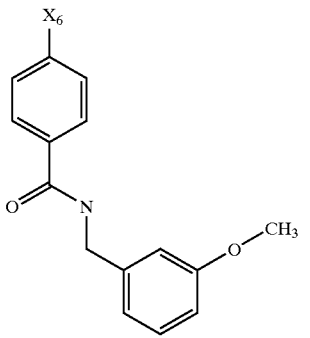 | |
| 140 | CH₃ X₂ | X₃―CH₃ (ethyl) | H | rac. | X₅―CH₂CH(CH₃)₂ (isopentyl) | 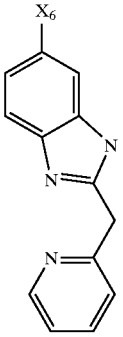 | 148 |
| 141 | X₂―CH₃ | H₃C―X₃ | H | rac. | (CH₃)₃C―CH₂―X₅ | 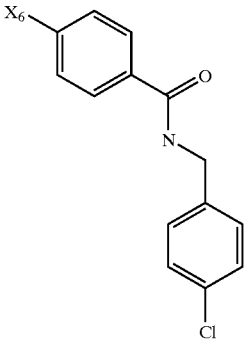 | |
| 142 | X₂―CH₃ | H₃C―X₃ | H | rac. | (CH₃)₃C―CH₂―X₅ | 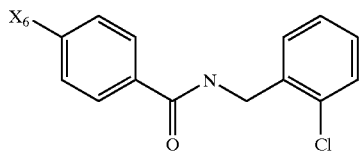 | |

TABLE 1-continued

| Ex. | R² | R³ | R⁴ | config. R³ or R⁴ | R⁵ | R⁶ | mp. [° C.] |
|---|---|---|---|---|---|---|---|
| 143 | CH₃ X₂ | X₃—CH₃ | H | rac. | X₅—CH₂CH₂C(CH₃)₃ | X₆—C₆H₃(OCH₃)—C(O)NH—C₆H₄—OCH₃ | 186 |
| 144 | CH₃ X₂ | X₃—X₄ (azetidine) | | | X₅—CH₂CH₂CH(CH₃)₂ | X₆—C₆H₃(OCH₃)—C(O)NH-cyclobutyl | 199 |
| 145 | CH₃ X₂ | X₃—CH₃ | H | rac. | X₅—CH₂-cyclopropyl | X₆—C₆H₄—C(O)NH—CH₂—C₆H₄—C(O)OCH₃ | 214 |
| 146 | CH₃ X₂ | X₃—CH₃ | H | rac. | X₅—CH₂-cyclopropyl | X₆—C₆H₄—C(O)NH—CH₂CH₂-(2-benzimidazolyl) | 155 |

TABLE 1-continued

| Ex. | R² | R³ | R⁴ | config. R³ or R⁴ | R⁵ | R⁶ | mp. [° C.] |
|---|---|---|---|---|---|---|---|
| 147 | CH₃—X₂ | X₃—CH₂—CH₃ | H | rac. | X₅—CH₂—CH(CH₃)—CH₃ | X₆—C₆H₄—C(O)NH—CH₂—(2-pyridyl) | |
| 148 | X₂—CH(CH₃)₂ | H₃C—X₃ | H | rac. | H₃C—C(CH₃)₂—CH₂—X₅ | X₆—C₆H₄—C(O)NH₂ | |
| 149 | X₂—CH(CH₃)₂ | X₃—CH₃ | H | rac. | CH₃—(CH₂)₃—X₅ | cyclohexyl-CH₂—NH—C(O)—C₆H₄—X₆ | 245 |
| 150 | CH₃—X₂ | X₃—CH₃ | H | rac. | H₃C—CH(CH₂CH₃)—CH₂—X₅ | X₆—C₆H₄—C(O)NH—CH₂—C₆H₅ | |
| 151 | CH₃—X₂ | X₃—CH₂—CH₃ | H | rac. | X₅—CH₂—CH₂—CH(CH₃)—CH₃ | (6-chloro-2-methylpyridin-3-yl)—CH₂—NH—C(O)—C₆H₄—X₆ | |

TABLE 1-continued

| Ex. | R² | R³ | R⁴ | config. R³ or R⁴ | R⁵ | R⁶ | mp. [° C.] |
|---|---|---|---|---|---|---|---|
| 152 | CH₃–X₂ | X₃–CH₃ | H | rac. | X₅–CH₂CH₂–CH(CH₃)₂ (isopentyl) | 3,5-difluoro-4-hydroxybenzyl-NH-C(O)-C₆H₄-X₆ | |
| 153 | X₂–CH(CH₃)₂ (isopropyl on N) | X₃–CH₃ | H | rac. | X₅–(CH₂)₃–CH₃ (pentyl) | 5-amino-pyridin-2-yl-NH-CH₂CH₂-N(H)-C(O)-C₆H₄-X₆ | |
| 154 | CH₃–X₂ | X₃–CH₃ | H | rac. | X₅–CH₂–cyclopropyl | X₆-C₆H₄-C(O)-NH-CH(CH₂CH₃)(C₆H₅) | |
| 155 | X₂–CH(CH₃)₂ | H₃C–X₃ | H | rac. | X₅–CH₂–C(CH₃)₃ (neopentyl) | X₆-C₆H₄-C(O)-NH-CH₂-(2-hydroxy-6-methyl-pyridin-3-yl) | |

TABLE 1-continued

| Ex. | R² | R³ | R⁴ | config. R³ or R⁴ | R⁵ | R⁶ | mp. [° C.] |
|---|---|---|---|---|---|---|---|
| 156 | CH₃, X₂ | X₃—CH₂—CH₃ | H | rac. | X₅—CH(CH₃)—CH(CH₃)—CH₃ | X₆—C₆H₄—C(O)—NH—CH₂—C₆H₅ | 265 |
| 157 | CH₃, X₂ | X₃—CH₃ | H | rac. | X₅—CH₂-cyclopropyl | X₆—C₆H₄—C(O)—NH—CH₂CH₂-(1-methylpyrrol-2-yl) | 192 |
| 158 | CH₃, X₂ | X₃—CH₃ | H | rac. | X₅—CH₂CH₂—CH(CH₃)₂ | pyridin-4-yl—N—C(O)—C₆H₄—X₆ | 222 |
| 159 | CH₃, X₂ | X₃—CH₃ | H | rac. | X₅—CH₂CH₂—CH(CH₃)₂ | (6-chloropyridin-3-yl)—N—C(O)—C₆H₄—X₆ | 221 |
| 160 | X₂, CH₃ | X₃—CH₃ | X₄—CH₃ |  | (CH₃)₂CH—CH₂—CH₂—X₆ (with CH₃ branch) | X₆—C₆H₄—C(O)—NH₂ | 298 |

TABLE 1-continued

| Ex. | R² | R³ | R⁴ | config. R³ or R⁴ | R⁵ | R⁶ | mp. [° C.] |
|---|---|---|---|---|---|---|---|
| 161 | CH₃, X₂ | X₃—CH₃ | H | rac. | X₅—CH₂—cyclopropyl | X₆—C₆H₄—C(O)NH—CH₂-(2-pyridyl) | 181 |
| 162 | X₂, CH₃ | X₃—CH₃ | H | S | isopentyl (H₃C-CH(CH₃)-CH₂-CH₂-X₅) | 3-methoxy-4-X₆-C₆H₃-C(O)NH-CH₂-(3-pyridyl) | — |
| 163 | CH₃, X₂ | azetidine (X₃—X₄) | | | X₅-CH₂-CH(CH₃)-CH₃ | 3-methoxy-4-X₆-C₆H₃-C(O)NH-CH₂-cyclopropyl | 172 |
| 164 | CH₃, X₂ | X₃—CH₃ | H | rac. | X₅-CH₂-CH₂-C(CH₃)₂-CH₃ | X₆-C₆H₄-C(O)NH-CH₂-C(CH₃)₃ | 227 |

TABLE 1-continued

[Structure: pteridinone core with substituents R2, R3, R4, R5, R6 as labeled]

| Ex. | R² | R³ | R⁴ | config. R³ or R⁴ | R⁵ | R⁶ | mp. [° C.] |
|---|---|---|---|---|---|---|---|
| 165 | CH₃, X₂ | X₃—CH₃ | H | rac. | X₅—CH₂CH₂CH(CH₃)₂ (isopentyl) | [3-({[4-X₆-benzoyl]amino}methyl)-6-methyl-2-hydroxypyridine] | 258 |
| 166 | CH₃, X₂ | X₃—CH₃ | X₄—CH₃ |  | X₅—CH₂CH₂CH(CH₃)₂ | [4-X₆-N-isopropyl-benzamide linked via benzoyl] | 266 |
| 167 | X₂—CH₃, CH₃ | H₃C—X₃ | H | rac. | [neopentyl with X₅: H₃C-C(CH₃)₂-CH₂-X₅] with extra CH₃ | [4-X₆-C₆H₄-C(=O)-NH-CH₂-C₆H₄-C(=O)-NH₂] | — |
| 168 | CH₃, X₂ | X₃—CH₃ | X₄—CH₃ | rac. | X₅—CH₂CH₂CH(CH₃)₂ | [N-(pyridin-3-yl)-4-X₆-3-methoxy-benzamide] | 159 |
| 169 | CH₃, X₂ | [azetidine: X₃—X₄ cyclobutane-like] |  |  | X₅—CH₂CH₂CH(CH₃)₂ | [N-cyclopropyl-3-methoxy-4-X₆-benzamide] | 250 |

TABLE 1-continued

| Ex. | R² | R³ | R⁴ | config. R³ or R⁴ | R⁵ | R⁶ | mp. [° C.] |
|---|---|---|---|---|---|---|---|
| 170 | CH₃, X₂ | X₃—CH₃ | H | rac. | X₅—CH₂—cyclopropyl | X₆—C₆H₄—C(O)NH—CH₂—(4-pyridyl) | 213 |
| 171 | CH₃, X₂ | X₃—CH₃ | H | rac. | X₅—CH₂CH₂—CH(CH₃)₂ | benzyl-NH—C(O)—C₆H₄—X₆ | 228 |
| 172 | CH₃, X₂ | X₃—CH₃ | H | rac. | X₅—CH₂-cyclopropyl | X₆—C₆H₄—C(O)NH—CH₂—(5-methylpyrazin-2-yl) | 181 |
| 173 | CH₃, X₂ | X₃—CH₃ | H | rac. | X₅—CH₂-cyclopropyl | X₆—C₆H₄—C(O)NH—CH₂—C₆H₄—CH₂—(4-methylpiperazin-1-yl) | 182 |

TABLE 1-continued
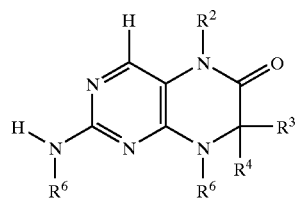
| Ex. | R² | R³ | R⁴ | config. R³ or R⁴ | R⁵ | R⁶ | mp. [° C.] |
|---|---|---|---|---|---|---|---|
| 174 | X₂—CH₃ (CH₃) | H₃C—X₃ | H | rac. | (CH₃)₃C—CH₂—X₅ | X₆—C₆H₄—C(O)—NH—C₆H₅ | |
| 175 | CH₃—X₂ (CH₃) | X₃—CH₂—CH₃ | H | rac. | X₅—CH(CH₃)—CH(CH₃)₂ | X₆—C₆H₄—C(O)—NH—CH₂-(2-pyridyl) | 197 |
| 176 | X₂—CH₃ (CH₃) | H₃C—X₃ | H | rac. | (CH₃)₃C—CH₂—X₅ | X₆—C₆H₄—C(O)—NH-(4-pyridyl) | |
| 177 | CH₃—X₂ (CH₃) | X₃—CH₂—CH₃ | H | rac. | X₅—CH(CH₃)—CH(CH₃)₂ | X₆—C₆H₄—C(O)—NH—CH₂-(4-pyridyl) | 216 |

TABLE 1-continued

| Ex. | R² | R³ | R⁴ | config. R³ or R⁴ | R⁵ | R⁶ | mp. [° C.] |
|---|---|---|---|---|---|---|---|
| 178 | CH₃, X₂ | X₃–CH₃ | H | rac. | X₅–CH₂CH₂–cyclopropyl | X₆–(4-phenyl)–C(O)–NH–CH₂–(2-pyridyl) | 200 |
| 179 | CH₃, X₂ | X₃–CH₃ | H | rac. | X₅–CH₂–cyclopropyl | X₆–(4-phenyl)–C(O)–NH–CH₂–(2-thienyl) | 197 |
| 180 | CH₃, X₂ | X₃–CH₃ | X₄–CH₃ | rac. | X₅–CH₂–CH(CH₃)₂ | (4-pyridyl)–NH–C(O)–(3-methoxy-4-X₆-phenyl) | 143 |
| 181 | CH₃, X₂ | X₃–(cyclopropyl)–X₄ | | | X₅–CH₂CH₂–CH(CH₃)₂ | (3-methoxy-4-X₆-phenyl)–C(O)–NH–CH(CH₃)₂ | 234 |

TABLE 1-continued
| Ex. | R² | R³ | R⁴ | config. R³ or R⁴ | R⁵ | R⁶ | mp. [° C.] |
|---|---|---|---|---|---|---|---|
| 182 | X₂—CH₃ | H₃C—X₃ | H | rac. | (CH₃)₃C-CH₂-X₅ | X₆-C₆H₄-C(O)-NH-CH₂-(3-C(O)NH₂-C₆H₄) | |
| 183 | CH₃—X₂ | X₃—CH₃ | H | rac. | X₅-CH₂-cyclopropyl | X₆-C₆H₄-C(O)-NH-CH₂-(4-(morpholinomethyl)-C₆H₄) | 169 |
| 184 | X₂—CH₃ | H₃C—X₃ | H | rac. | (CH₃)₃C-CH₂-X₅ | X₅-C₆H₄-C(O)-NH-CH₂-(3-Cl-C₆H₄) | |
| 185 | CH₃—X₂ | X₃—CH₃ | H | rac. | X₃-CH₂-cyclohexyl | PhCH₂-N(H)-C(O)-C₆H₄-X₆ | 198 |

TABLE 1-continued
| Ex. | R² | R³ | R⁴ | config. R³ or R⁴ | R⁵ | R⁶ | mp. [° C.] |
|---|---|---|---|---|---|---|---|
| 186 | CH₃–X₂ | X₃–X₄ (azetidine) | | | isopentyl (X₅CH₂CH₂CH(CH₃)₂) | 4-methoxy-3-(N-methylcarbamoyl)phenyl-X₆ | 202 |
| 187 | CH₃–X₂ | X₃–CH₃ | H | rac. | X₅–CH₂–cyclopropyl | 4-(N-indan-1-yl-carbamoyl)phenyl-X₆ | 200 |
| 188 | CH₃–X₂ | X₃–CH₃ | H | rac. | X₅–CH₂–cyclopropyl | 4-(N-(pyridin-4-ylmethyl)carbamoyl)phenyl-X₆ | 198 |
| 189 | CH₃–X₂ | X₃–CH₃ | H | rac. | X₅–CH₂–cyclopropyl | 4-(N-(2-cyanoethyl)carbamoyl)phenyl-X₆ | 198 |

TABLE 1-continued

| Ex. | R² | R³ | R⁴ | config. R³ or R⁴ | R⁵ | R⁶ | mp. [° C.] |
|---|---|---|---|---|---|---|---|
| 190 | CH₃, X₂ | X₃, X₄ (cyclobutyl) | | | X₅–CH₂CH(CH₃)₂ (isobutyl via CH₂) | X₆-(3-methoxy-4-methoxy-phenyl carboxamide) | 196 |
| 191 | CH₃, X₂ | X₃—CH₃ | X₄—CH₃ | | X₅–CH₂CH(CH₃)₂ | X₆-phenyl-C(O)NH-cyclobutyl | 253 |
| 192 | X₂, CH₃ | H₃C—CH₂CH₂—X₃ | H | rac. | cyclopropylmethyl–X₅ | X₆-phenyl-C(O)NH-CH₂-(2-chloro-4,6-dimethylpyridin-3-yl) | — |
| 193 | CH₃, X₂ | X₃—CH₃ | H | rac. | cyclopropylmethyl–X₅ | X₆-phenyl-C(O)NH-CH₂-(1,3-dimethyl-1H-pyrazol-4-yl) | 201 |

US 6,806,272 B2
115                                                                                                                    116
TABLE 1-continued
| Ex. | R² | R³ | R⁴ | config. R³ or R⁴ | R⁵ | R⁶ | mp. [° C.] |
|---|---|---|---|---|---|---|---|
| 194 | CH₃ X₂ | X₃ CH₃ | H | rac. |  | 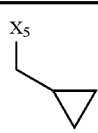 | 250 |
| 195 | CH₃ X₂ | X₃ CH₃ | H | rac. | 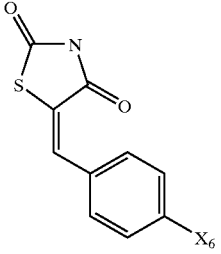 |  | 198 |
| 196 | CH₃ X₂ | X₃ CH₃ | H | rac. |  | 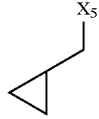 | 245 |
| 197 | X₂ CH₃ | X₃ CH₃ | H | rac. | 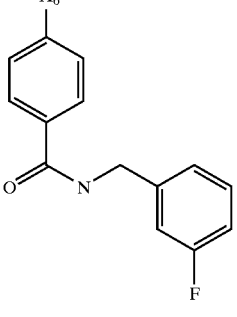 |  | |

TABLE 1-continued
| Ex. | R² | R³ | R⁴ | config. R³ or R⁴ | R⁵ | R⁶ | mp. [° C.] |
|---|---|---|---|---|---|---|---|
| 198 | X₂–CH₃ | H₃C–X₃ | H | rac. | neopentyl-X₅ (H₃C)₃C-CH₂-X₅ | 4-(2-(trifluoromethoxy)benzylcarbamoyl)phenyl-X₆ | |
| 199 | CH₃, X₂ | X₃–CH₃ | H | rac. | cyclopropylmethyl-X₅ | 4-(1-phenylethylcarbamoyl)phenyl-X₆ | |
| 200 | CH₃, X₂ | X₃–CH₃ | X₄–CH₃ | | isopentyl-X₅ | 4-(cyclobutylcarbamoyl)-3-methoxyphenyl-X₆ | 198 |
| 201 | X₂–CH₃ | H | H | rac. | 4-acetoxybutyl-X₅ | 4-(benzylcarbamoyl)phenyl-X₆ | |

TABLE 1-continued

| Ex. | R² | R³ | R⁴ | config. R³ or R⁴ | R⁵ | R⁶ | mp. [° C.] |
|---|---|---|---|---|---|---|---|
| 202 | X₂, CH₃ | H₃C—X₃ | H | rac. | H₃C-CH(CH₃)-CH₂-CH₂-X₅ | X₆-C₆H₄-C(O)NH₂ | |
| 203 | CH₃, X₂ | X₃—CH₃ | H | rac. | cyclopropyl-CH₂-X₅ | X₆-C₆H₄-C(O)NH-CH₂-(3-methoxyphenyl) | 198 |
| 204 | X₂, CH₃ | H₃C-CH₂-CH₂-X₃ | H | rac. | cyclopropyl-CH₂-X₅ | X₆-C₆H₄-C(O)NH-CH₂-C₆H₅ | |
| 205 | X₂, CH₃ | H₃C-CH₂-CH₂-X₃ | H | rac. | cyclopropyl-CH₂-X₅ | X₆-C₆H₄-C(O)NH-CH₂-(2-methyl-6-chloropyridin-3-yl) | |

TABLE 1-continued

| Ex. | R² | R³ | R⁴ | config. R³ or R⁴ | R⁵ | R⁶ | mp. [° C.] |
|---|---|---|---|---|---|---|---|
| 206 | X₂—CH₃ | H₃C—X₃ | H | rac. | cyclopropylmethyl-X₅ | 3-methoxy-4-X₆-benzoyl-N-(pyridin-4-yl) | |
| 207 | CH₃—X₂ | X₃—CH₃ | H | rac. | cyclopropylmethyl-X₅ | 4-X₆-benzoyl-N-(2-aminobenzyl) | 184 |
| 208 | X₂—CH₃ | X₃—CH₃ | H | rac. | n-butyl-X₅ | N-benzyl-4-X₆-benzamide | 253 |
| 209 | CH₃—X₂ | X₃—CH₃ (ethyl) | H | rac. | cyclopropylmethyl-X₅ | methyl 4-X₆-benzoate | 240 |
| 210 | X₂—CH₃ | H₃C—X₃ | H | rac. | neopentyl-X₅ | 4-X₆-N-(4-trifluoromethylbenzyl)benzamide | |

TABLE 1-continued

| Ex. | R² | R³ | R⁴ | config. R³ or R⁴ | R⁵ | R⁶ | mp. [° C.] |
|---|---|---|---|---|---|---|---|
| 211 | CH₃, X₂ | X₃—CH₃ | X₄—CH₃ | | X₅—CH₂CH₂—CH(CH₃)₂ (isopentyl) | X₆-C₆H₄-C(O)N(H)CH₃ (4-position) | 266 |
| 212 | CH₃, X₂ | X₃—CH₂CH₃ | H | rac. | X₅—CH₂CH₂—CH(CH₃)₂ | X₆-C₆H₃(2-F)(4-Cl) | |
| 213 | CH₃, X₂ | X₃—CH₃ | H | rac. | X₅—CH₂CH₂CH₂CH₃ | X₆-C₆H₄-C(O)N(H)CH₂-(5-methylpyrazin-2-yl) (3-position) | |
| 214 | CH₃, X₂ | X₃—CH₃ | H | rac. | X₅—CH₂CH₂-cyclopropyl | X₆-C₆H₄-C(O)OH (4-position) | |
| 215 | CH₃, X₂ | X₃—CH₃ | H | rac. | X₅—CH₂-cyclohexyl | HO-C₆H₄-X₆ (4-hydroxyphenyl) | 232 |

TABLE 1-continued

| Ex. | R² | R³ | R⁴ | config. R³ or R⁴ | R⁵ | R⁶ | mp. [° C.] |
|---|---|---|---|---|---|---|---|
| 216 | CH₃–X₂ | X₃–CH₃ | H | rac. | X₅–CH₂CH(CH₃)₂ | X₆–(3-pyridylmethylaminocarbonyl)phenyl | |
| 217 | X₂–CH₃ | H₃C–X₃ | H | rac. | neopentyl (H₃C)₃C-CH₂-X₅ | X₆–phenyl-C(O)NH-CH₂-(3-OCHF₂-phenyl) | |
| 218 | X₂–CH₃ | H₃C–X₃ | H | rac. | neopentyl (H₃C)₃C-CH₂-X₅ | X₆–(3,5-difluoro-4-hydroxyphenyl) | >250 |
| 219 | CH₃–X₂ | H₃C–X₃ | H | rac. | X₅–CH₂CH₂CH(CH₃)₂ | 2,6-difluoro-4-X₆-phenol | 260 (Zers.) |
| 220 | X₂–CH₃ | H₃C–X₃ | H | R | H₃C-CH(CH₃)-CH₂CH₂-X₅ | X₆–(3-methoxy-4-carboxamidophenyl) | 190 |

TABLE 1-continued

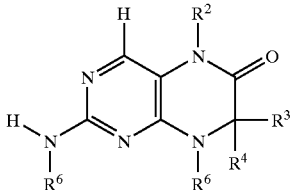

| Ex. | R² | R³ | R⁴ | config. R³ or R⁴ | R⁵ | R⁶ | mp. [° C.] |
|---|---|---|---|---|---|---|---|
| 221 | X₂–CH(CH₃)– | H₃C–CH(X₃)– | H | R | (CH₃)₂CH–CH₂–CH(X₅)– | 4-X₆-C₆H₄-C(O)NH₂ | 228 |
| 222 | X₂–CH(CH₃)– | H₃C–CH(X₃)– | H | R | (CH₃)₂CH–CH₂–CH(X₅)– | 4-X₆-2-Cl-C₆H₃-C(O)NH₂ | |
| 223 | CH₃–CH(X₂)– | X₃–CH(CH₃)–CH₂– | H | R | X₅–CH₂–CH₂–CH(CH₃)₂ alt. | 4-X₆-C₆H₄-C(O)NH₂ | 243 |
| 224 | CH₃–CH(X₂)– | X₃–CH(CH₃)–CH₂– | H | R | X₅–CH₂–CH₂–CH(CH₃)₂ alt. | 4-X₆-3-OCH₃-C₆H₃-C(O)NH₂ | 258 |
| 225 | X₂–CH(CH₃)– | H₃C–CH(X₃)– | H | R | (CH₃)₂CH–CH₂–CH(X₅)– | 4-X₆-2-CH₃-C₆H₃-C(O)NH₂ | |
| 226 | X₂–CH(CH₃)– | H₃C–CH(X₃)– | H | R | (CH₃)₂CH–CH₂–CH(X₅)– | 4-X₆-2-OCH₃-C₆H₃-C(O)NH₂ | |

TABLE 1-continued
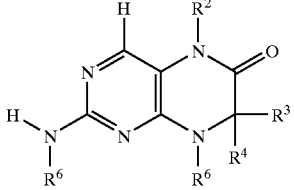
| Ex. | R² | R³ | R⁴ | config. R³ or R⁴ | R⁵ | R⁶ | mp. [° C.] |
|---|---|---|---|---|---|---|---|
| 227 | X₂—CH₃, CH₃ | H₃C—X₃ | H | R | H₃C—C(CH₃)₂—CH₂—X₅ | X₆—(4-)—3-OCH₃—C₆H₃—C(O)NH₂ | 241 |
| 228 | X₂—CH₃, CH₃ | H₃C—X₃ | H | R | H₃C—C(CH₃)₂—CH₂—X₅ | X₆—C₆H₄—C(O)NH₂ | — |
| 229 | CH₃, X₂ | H₃C—X₃ | H | R | X₅—CH(CH₃)₂ | X₆—C₆H₄—C(O)NH₂ | 300 |
| 230 | CH₃, X₂ | H₃C—X₃ | H | R | X₅—CH(CH₃)₂ | X₆—(4-)—3-OCH₃—C₆H₃—C(O)NH₂ | 200 |
| 231 | CH₃, X₂ | X₃—CH₂CH₃ | H | R | X₅—CH(CH₃)₂ | X₆—C₆H₄—C(O)NH₂ | 232 |
| 232 | CH₃, X₂ | X₃—CH₂CH₃ | H | R | X₅—CH(CH₃)₂ | X₆—(4-)—3-OCH₃—C₆H₃—C(O)NH₂ | 149 |

TABLE 1-continued

| Ex. | R² | R³ | R⁴ | config. R³ or R⁴ | R⁵ | R⁶ | mp. [° C.] |
|---|---|---|---|---|---|---|---|
| 234 | CH₃ \| X₂ | H₃C—X₃ | H | R | cyclopentyl-X₅ | 4-carbamoyl-2-methoxyphenyl-X₆ | 197 |
| 235 | CH₃ \| X₂ | H₃C—X₃ | H | R | cyclopentyl-X₅ | 4-carbamoylphenyl-X₆ | 226 |
| 236 | CH₃ \| X₂ | H₃C—X₃ | H | R | cyclobutyl-X₅ | 4-carbamoyl-2-methoxyphenyl-X₆ | 182 |
| 237 | CH₃ \| X₂ | H₃C—X₃ | H | R | cyclopropyl-X₅ | 4-carbamoyl-3-methoxyphenyl-X₆ | |
| 238 | CH₃ \| X₂ | X₃—CH₂—CH₃ | H | R | cyclopentyl-X₅ | 4-carbamoylphenyl-X₆ | |

TABLE 1-continued

| Ex. | R² | R³ | R⁴ | config. R³ or R⁴ | R⁵ | R⁶ | mp. [° C.] |
|---|---|---|---|---|---|---|---|
| 239 | CH₃, X₂ | X₃―CH₃ (ethyl) | H | R | cyclopentyl-X₅ | 4-(H₃CO)-3-(H₂NC(O))-phenyl-X₆ (methoxy/carbamoyl benzene) | |
| 240 | CH₃, X₂ | H₃C―X₃ | H | R | cyclopentyl-X₅ | 4-CH₃-3-(H₂NC(O))-phenyl-X₆ | |
| 241 | CH₃, X₂ | H₃C―X₃ | H | R | cyclohexyl-X₅ | 3-OCH₃-4-X₆-phenyl-C(O)NH₂ | 194 |
| 242 | CH₃, X₂ | H₃C―X₃ | H | R | cyclobutyl-X₅ | 4-X₆-phenyl-C(O)NH₂ | 200 |
| 243 | CH₃, X₂ | H₃C―X₃ | H | R | (CH₃)₂CH-CH₂-CH₂-X₅ (isopentyl) | N-cyclobutyl-3-methoxy-4-X₆-benzamide | 156 |

TABLE 1-continued

| Ex. | R² | R³ | R⁴ | config. R³ or R⁴ | R⁵ | R⁶ | mp. [° C.] |
|---|---|---|---|---|---|---|---|
| 244 | CH₃, X₂ | X₃—CH₃ (ethyl) | H | R | X₅-CH₂-CH₂-CH(CH₃)-CH₃ (isopentyl with X₅) | N-cyclobutyl benzamide, para-X₆ | 195 |
| 245 | CH₃, X₂ | X₃—CH₃ (ethyl) | H | R | X₅-CH₂-CH₂-CH(CH₃)-CH₃ | N-cyclobutyl-3-methoxy-4-X₆-benzamide | 147 |
| 246 | X₂, CH₃ | H₃C—X₃ | H | R | H₃C-CH(CH₃)-CH₂-CH₂-X₅ | 4-X₆-2-methoxy-N-cyclobutylbenzamide | — |
| 247 | CH₃, X₂ | H₃C—X₃ | H | R | X₅-CH₂-CH(CH₃)-CH₃ (isobutyl) | 3-methoxy-4-X₆-N-cyclobutylbenzamide | 85 |
| 248 | X₂, CH₃ | H₃C—X₃ | H | R | H₃C-C(CH₃)(CH₃)-CH₂-X₅ (neopentyl) | 4-X₆-N-cyclobutylbenzamide | — |

TABLE 1-continued

| Ex. | R² | R³ | R⁴ | config. R³ or R⁴ | R⁵ | R⁶ | mp. [° C.] |
|---|---|---|---|---|---|---|---|
| 249 | CH₃–X₂ | H₃C–X₃ | H | R | neopentyl (X₅–CH₂–C(CH₃)₃) | 4-(N-cyclobutylcarbamoyl)-2-methoxyphenyl (X₆) | |
| 250 | CH₃–X₂ | H₃C–X₃ | H | R | isobutyl (X₅–CH(CH₃)₂) | 4-(N-cyclobutylcarbamoyl)phenyl (X₆) | 158 |
| 251 | CH₃–X₂ | H₃C–X₃ | H | R | cyclopentyl (X₅) | 4-(N-cyclobutylcarbamoyl)-2-methoxyphenyl (X₆) | 188 |
| 252 | CH₃–X₂ | H₃C–X₃ | H | R | cyclopentyl (X₅) | 4-(N-cyclobutylcarbamoyl)phenyl (X₆) | 245 |

TABLE 1-continued

| Ex. | R² | R³ | R⁴ | config. R³ or R⁴ | R⁵ | R⁶ | mp. [° C.] |
|---|---|---|---|---|---|---|---|
| 253 | CH₃, X₂ | H₃C–X₃ | H | R | cyclopropyl (X₅) | 4-(N-cyclobutylcarbamoyl)phenyl (X₆) | |
| 254 | CH₃, X₂ | H₃C–X₃ | H | R | cyclobutyl (X₅) | 4-(N-cyclobutylcarbamoyl)phenyl (X₆) | 128 |
| 255 | CH₃, X₂ | H₃C–X₃ | H | R | cyclopropyl (X₅) | 4-(N-cyclobutylcarbamoyl)-3-methoxyphenyl (X₆) | |
| 256 | CH₃, X₂ | X₃–CH₂CH₃ | H | R | isopropyl (X₅) | 4-(N-cyclobutylcarbamoyl)phenyl (X₆) | 181 |

TABLE 1-continued

| Ex. | R² | R³ | R⁴ | config. R³ or R⁴ | R⁵ | R⁶ | mp. [° C.] |
|---|---|---|---|---|---|---|---|
| 257 | CH₃, X₂ | X₃-CH₃ (ethyl via X₃) | H | R | isobutyl (X₅-CH(CH₃)-CH₃) | 4-(X₆)-3-methoxyphenyl-C(O)-NH-cyclobutyl | 217 |
| 258 | CH₃, X₂ | H₃C-X₃ | H | R | cyclopentyl (X₅) | 4-(X₆)-3-methylphenyl-C(O)-NH-cyclobutyl | |
| 259 | CH₃, X₂ | H₃C-X₃ | H | R | cyclohexyl (X₅) | 4-(X₆)-3-methoxyphenyl-C(O)-NH-cyclobutyl | |
| 260 | CH₃, X₂ | H₃C-X₃ | H | R | cyclohexyl (X₅) | 4-(X₆)-phenyl-C(O)-NH-cyclobutyl | |
| 261 | X₂, CH₃ | H₃C-X₃ | H | R | isopentyl (H₃C-CH(CH₃)-CH₂-CH₂-X₅) | 4-(X₆)-phenyl-C(O)-NH-cyclopropyl | 230 |

TABLE 1-continued

| Ex. | R² | R³ | R⁴ | config. R³ or R⁴ | R⁵ | R⁶ | mp. [° C.] |
|---|---|---|---|---|---|---|---|
| 262 | X₂—CH(CH₃) | H₃C—X₃ | H | R | (CH₃)₂CHCH₂CH₂—X₅ | 3-methoxy-4-X₆-N-cyclopropylbenzamide | 193 |
| 263 | X₂—CH(CH₃) | H₃C—X₃ | H | R | (CH₃)₂CHCH₂CH₂—X₅ | 2-chloro-4-X₆-N-cyclopropylbenzamide | — |
| 264 | CH₃—CH(X₂) | X₃—CH₂CH₃ | H | R | X₅—CH₂CH₂CH(CH₃)₂ | 3-methoxy-4-X₆-N-cyclopropylbenzamide | 152 |
| 265 | CH₃—CH(X₂) | X₃—CH₂CH₃ | H | R | X₅—CH₂CH₂CH(CH₃)₂ | 4-X₆-N-cyclopropylbenzamide | 207 |
| 266 | X₂—CH(CH₃) | H₃C—X₃ | H | R | (CH₃)₂CHCH₂CH₂—X₅ | 4-X₆-2-methyl-N-cyclopropylbenzamide | 229 |

TABLE 1-continued

| Ex. | R² | R³ | R⁴ | config. R³ or R⁴ | R⁵ | R⁶ | mp. [° C.] |
|---|---|---|---|---|---|---|---|
| 267 | X₂—CH₃ | H₃C—X₃ | H | R | (CH₃)₂CHCH₂CH₂—X₅ (isopentyl) | 2-methoxy-4-X₆-N-cyclopropylbenzamide | |
| 268 | CH₃—X₂ | H₃C—X₃ | H | R | (CH₃)₂CHCH₂—X₅ (isobutyl) | 3-methoxy-4-X₆-N-cyclopropylbenzamide | 183 |
| 269 | X₂—CH₃ | H₃C—X₃ | H | R | neopentyl-X₅ | 3-methoxy-4-X₆-N-cyclopropylbenzamide | |
| 270 | X₂—CH₃ | H₃C—X₃ | H | R | neopentyl-X₅ | 4-X₆-N-cyclopropylbenzamide | 161 |
| 271 | CH₃—X₂ | H₃C—X₃ | H | R | (CH₃)₂CHCH₂—X₅ (isobutyl) | 4-X₆-N-cyclopropylbenzamide | 282 |

TABLE 1-continued

| Ex. | R² | R³ | R⁴ | config. R³ or R⁴ | R⁵ | R⁶ | mp. [° C.] |
|---|---|---|---|---|---|---|---|
| 272 | CH₃, X₂ | X₃—CH₂—CH₃ | H | R | (CH₃)₂CH—CH₂— (X₅) | 4-(cyclopropylaminocarbonyl)-2-methoxyphenyl (X₆) | 157 |
| 273 | CH₃, X₂ | X₃—CH₂—CH₃ | H | R | (CH₃)₂CH—CH₂— (X₅) | 4-(cyclopropylaminocarbonyl)phenyl (X₆) | 129 |
| 274 | CH₃, X₂ | H₃C—X₃ | H | R | cyclopentyl (X₅) | 4-(cyclopropylaminocarbonyl)-2-methoxyphenyl (X₆) | 164 |
| 275 | CH₃, X₂ | H₃C—X₃ | H | R | cyclopentyl (X₅) | 4-(cyclopropylaminocarbonyl)phenyl (X₆) | 219 |
| 276 | CH₃, X₂ | H₃C—X₃ | H | R | cyclopropyl (X₅) | 4-(cyclopropylaminocarbonyl)phenyl (X₆) | — |

TABLE 1-continued
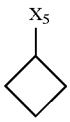
| Ex. | R² | R³ | R⁴ | config. R³ or R⁴ | R⁵ | R⁶ | mp. [° C.] |
|---|---|---|---|---|---|---|---|
| 277 | CH₃—X₂ | H₃C—X₃ | H | R | cyclobutyl-X₅ | 4-methoxy-3-(N-cyclopropylcarbamoyl)phenyl-X₆ | 200 |
| 278 | CH₃—X₂ | H₃C—X₃ | H | R | cyclobutyl-X₅ | 4-(N-cyclopropylcarbamoyl)phenyl-X₆ | 200 |
| 279 | CH₃—X₂ | H₃C—X₃ | H | R | cyclopropyl-X₅ | 4-methoxy-3-(N-cyclopropylcarbamoyl)phenyl-X₆ | |
| 280 | CH₃—X₂ | X₃—CH₂—CH₃ | H | R | cyclopentyl-X₅ | 3-methoxy-4-(N-cyclopropylcarbamoyl)phenyl-X₆ | |

TABLE 1-continued

| Ex. | R² | R³ | R⁴ | config. R³ or R⁴ | R⁵ | R⁶ | mp. [° C.] |
|-----|-----|-----|-----|-----|-----|-----|-----|
| 281 | CH₃, X₂ | X₃-CH₂-CH₃ | H | R | cyclopentyl-X₅ | 4-(N-cyclopropylcarbamoyl)phenyl-X₆ | |
| 282 | CH₃, X₂ | H₃C-X₃ | H | R | cyclopentyl-X₅ | 3-methyl-4-(N-cyclopropylcarbamoyl)phenyl-X₆ | |
| 283 | CH₃, X₂ | H₃C-X₃ | H | R | isopentyl-X₅ | 3,5-dimethyl-4-(N-cyclopropylcarbamoyl)phenyl-X₆ | 277 |
| 284 | CH₃, X₂ | H₃C-X₃ | H | R | cyclohexyl-X₅ | 3-methoxy-4-(N-cyclopropylcarbamoyl)phenyl-X₆ | 197 |
| 285 | CH₃, X₂ | H₃C-X₃ | H | R | cyclohexyl-X₅ | 4-(N-cyclopropylcarbamoyl)phenyl-X₆ | |

TABLE 1-continued

| Ex. | R² | R³ | R⁴ | config. R³ or R⁴ | R⁵ | R⁶ | mp. [° C.] |
|---|---|---|---|---|---|---|---|
| 286 | CH₃, X₂ | H₃C-X₃ | H | R | X₅-CH(CH₃)-CH₃ | 3-methoxy-4-X₆-N-methylbenzamide | 182 |
| 287 | X₂, CH₃ | H₃C-X₃ | H | R | H₃C-CH(CH₃)-X₅ | 3-methoxy-4-X₆-N,N-dimethylbenzamide | |
| 288 | CH₃, X₂ | X₃-CH₂-CH₃ | H | R | X₅-CH(CH₃)-CH₃ | 2-methoxy-4-X₆-N-methylbenzamide | 163 |
| 289 | CH₃, X₂ | X₃-CH₂-CH₃ | H | R | X₅-CH(CH₃)-CH₃ | 4-X₆-N-methylbenzamide | 212 |
| 290 | X₂, CH₃ | H₃C-X₃ | H | R | H₃C-CH(CH₃)-X₅ | 4-X₆-2-methoxy-N-methylbenzamide | |

TABLE 1-continued

[Structure: pteridinone core with substituents R², R³, R⁴, R⁵, R⁶ as shown]

| Ex. | R² | R³ | R⁴ | config. R³ or R⁴ | R⁵ | R⁶ | mp. [° C.] |
|---|---|---|---|---|---|---|---|
| 291 | CH₃, X₂ | H₃C-X₃ | H | R | X₅-CH₂-C(CH₃)₃ (neopentyl) | 4-X₆-3-methoxyphenyl-C(=O)-NH-CH₃ | |
| 292 | X₂, CH₃ | H₃C-X₃ | H | R | H₃C-C(CH₃)₂-CH₂-X₅ | 4-X₆-phenyl-C(=O)-NH-CH₃ | |
| 293 | CH₃, X₂ | H₃C-X₃ | H | R | X₅-CH(CH₃)₂ (isobutyl) | 4-X₆-3-methoxyphenyl-C(=O)-NH-CH₃ | 200 |
| 294 | CH₃, X₂ | X₃-CH₂-CH₃ | H | R | X₅-CH(CH₃)₂ | 4-X₆-phenyl-C(=O)-NH-CH₃ | 144 |
| 295 | CH₃, X₂ | H₃C-X₃ | H | R | X₅-cyclopentyl | 4-X₆-3-methoxyphenyl-C(=O)-NH-CH₃ | 221 |

TABLE 1-continued

| Ex. | R² | R³ | R⁴ | config. R³ or R⁴ | R⁵ | R⁶ | mp. [° C.] |
|---|---|---|---|---|---|---|---|
| 296 | CH₃–X₂ | H₃C–X₃ | H | R | X₅–cyclopentyl | X₆–C₆H₄–C(O)N(CH₃)H (para) | 150 |
| 297 | CH₃–X₂ | H₃C–X₃ | H | R | X₅–cyclopropyl | X₆–C₆H₄–C(O)N(CH₃)H (para) | |
| 298 | CH₃–X₂ | X₃–CH₂CH₃ | H | R | X₅–CH(CH₃)₂ | X₆–C₆H₃(OCH₃)–C(O)N(CH₃)H | 163 |
| 299 | CH₃–X₂ | H₃C–X₃ | H | R | X₅–cyclobutyl | X₆–C₆H₃(OCH₃)–C(O)N(CH₃)H | |
| 300 | CH₃–X₂ | H₃C–X₃ | H | R | X₅–cyclobutyl | X₆–C₆H₄–C(O)N(CH₃)H (para) | 98 |

TABLE 1-continued

| Ex. | R² | R³ | R⁴ | config. R³ or R⁴ | R⁵ | R⁶ | mp. [° C.] |
|---|---|---|---|---|---|---|---|
| 301 | CH₃–X₂ | H₃C–X₃ | H | R | cyclopropyl-X₅ | 4-(X₆)-3-methoxy-N-methylbenzamide | |
| 302 | CH₃–X₂ | X₃–CH₂CH₃ | H | R | cyclopentyl-X₅ | 4-(X₆)-N-methylbenzamide | |
| 303 | CH₃–X₂ | X₃–CH₂CH₃ | H | R | cyclopentyl-X₅ | 4-(X₆)-3-methoxy-N-methylbenzamide | |
| 304 | CH₃–X₂ | H₃C–X₃ | H | R | cyclopentyl-X₅ | 4-(X₆)-3-methyl-N-methylbenzamide | |
| 305 | CH₃–X₂ | H₃C–X₃ | H | R | cyclohexyl-X₅ | 4-(X₆)-N-methylbenzamide | |

TABLE 1-continued
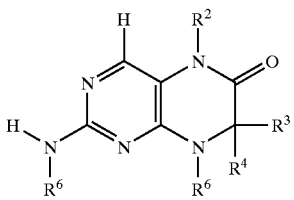
| Ex. | R² | R³ | R⁴ | config. R³ or R⁴ | R⁵ | R⁶ | mp. [° C.] |
|---|---|---|---|---|---|---|---|
| 306 | CH₃ X₂ | H₃C–X₃ | H | R | cyclohexyl-X₅ | 3-methoxy-4-X₆-N-methylbenzamide | |
| 307 | CH₃ X₂ | H₃C–X₃ | H | R | X₅–CH₂CH₂CH(CH₃)₂ | 3-methoxy-4-X₆-N-isopropylbenzamide | 179 |
| 308 | CH₃ X₂ | X₃–CH₂CH₃ | H | R | X₅–CH₂CH₂CH(CH₃)₂ | 4-X₆-3-methoxy-N-isopropylbenzamide | 174 |
| 309 | CH₃ X₂ | X₃–CH₂CH₃ | H | R | X₅–CH₂CH₂CH(CH₃)₂ | 4-X₆-N-isopropylbenzamide | 231 |

TABLE 1-continued

[Structure: pteridinone core with substituents R2, R3, R4, R5, R6, and NHR6 group]

| Ex. | R² | R³ | R⁴ | config. R³ or R⁴ | R⁵ | R⁶ | mp. [° C.] |
|---|---|---|---|---|---|---|---|
| 310 | CH₃, X₂ | H₃C–X₃ | H | R | isobutyl (X₅ on CH) | 3-methoxy-4-X₆-benzamide N-isopropyl | |
| 311 | X₂, CH₃ | H₃C–X₃ | H | R | isopentyl with X₅ | 4-X₆-2-methoxy-benzamide N-isopropyl | |
| 312 | X₂, CH₃ | H₃C–X₃ | H | R | neopentyl with X₅ | 4-X₆-benzamide N-isopropyl | |
| 313 | CH₃, X₂ | H₃C–X₃ | H | R | X₅-CH₂-C(CH₃)₃ neopentyl | 4-X₆-3-methoxy-benzamide N-isopropyl | |
| 314 | CH₃, X₂ | X₃-CH₂-CH₃ | H | R | isobutyl (X₅) | 4-X₆-3-methoxy-benzamide N-isopropyl | 69 |

TABLE 1-continued

| Ex. | R² | R³ | R⁴ | config. R³ or R⁴ | R⁵ | R⁶ | mp. [° C.] |
|---|---|---|---|---|---|---|---|
| 315 | CH₃ (X₂) | H₃C-X₃ | H | R | isopropyl (X₅) | 4-(N-isopropylcarbamoyl)phenyl (X₆) | 200 |
| 316 | CH₃ (X₂) | H₃C-X₃ | H | R | cyclopentyl (X₅) | 3-methoxy-4-(N-isopropylcarbamoyl)phenyl (X₆) | 210 |
| 317 | CH₃ (X₂) | H₃C-X₃ | H | R | cyclopentyl (X₅) | 4-(N-isopropylcarbamoyl)phenyl (X₆) | 131 |
| 318 | CH₃ (X₂) | H₃C-X₃ | H | R | cyclopropyl (X₅) | 4-(N-isopropylcarbamoyl)phenyl (X₆) | 131 |
| 319 | CH₃ (X₂) | H₃C-X₃ | H | R | cyclobutyl (X₅) | 4-(N-isopropylcarbamoyl)phenyl (X₆) | 145 |

TABLE 1-continued

| Ex. | R² | R³ | R⁴ | config. R³ or R⁴ | R⁵ | R⁶ | mp. [° C.] |
|---|---|---|---|---|---|---|---|
| 320 | CH₃ X₂ | H₃C—X₃ | H | R | cyclobutyl-X₅ | 4-X₆-3-methoxy-N-isopropylbenzamide | |
| 321 | CH₃ X₂ | H₃C—X₃ | H | R | cyclopropyl-X₅ | 4-X₆-3-methoxy-N-isopropylbenzamide | |
| 322 | CH₃ X₂ | X₃—CH₂—CH₃ | H | R | isopropyl-X₅ | 4-X₆-N-isopropylbenzamide | 149 |
| 323 | CH₃ X₂ | X₃—CH₂—CH₃ | H | R | cyclopentyl-X₅ | 4-X₆-N-isopropylbenzamide | |

TABLE 1-continued

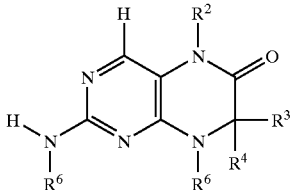

| Ex. | R² | R³ | R⁴ | config. R³ or R⁴ | R⁵ | R⁶ | mp. [° C.] |
|---|---|---|---|---|---|---|---|
| 324 | CH₃, X₂ | X₃─CH₃ (ethyl) | H | R | cyclopentyl-X₅ | 4-X₆-3-methoxy-N-isopropylbenzamide | |
| 325 | CH₃, X₂ | H₃C─X₃ | H | R | cyclopentyl-X₅ | 4-X₆-3-methyl-N-isopropylbenzamide | |
| 326 | CH₃, X₂ | H₃C─X₃ | H | R | cyclohexyl-X₅ | 4-X₆-3-methoxy-N-isopropylbenzamide | |
| 327 | CH₃, X₂ | H₃C─X₃ | H | R | cyclohexyl-X₅ | 4-X₆-N-isopropylbenzamide | |
| 328 | X₂─CH₃ | H₃C─X₃ | H | R | 4-methyl-3-methylpentyl-X₅ | 4-X₆-N-tert-butylbenzamide | 176 |

TABLE 1-continued

[Structure: pteridinone core with substituents R², R³, R⁴, R⁵, R⁶ as shown in header]

| Ex. | R² | R³ | R⁴ | config. R³ or R⁴ | R⁵ | R⁶ | mp. [° C.] |
|---|---|---|---|---|---|---|---|
| 329 | X₂—CH(CH₃) | H₃C—X₃ | H | R | (CH₃)₂CHCH₂CH₂—X₅ | 4-X₆-3-methoxy-C₆H₃-C(O)NH-C(CH₃)₃ | |
| 330 | X₂—CH(CH₃) | H₃C—X₃ | H | R | (CH₃)₂CHCH₂CH₂—X₅ | 4-X₆-2-chloro-C₆H₃-C(O)NH-C(CH₃)₃ | |
| 331 | CH₃, X₂ | X₃—CH₂CH₃ | H | R | X₅—CH₂CH₂—CH(CH₃)₂ | 4-X₆-3-methoxy-C₆H₃-C(O)NH-C(CH₃)₃ | |
| 332 | CH₃, X₂ | X₃—CH₂CH₃ | H | R | X₅—CH₂CH₂—CH(CH₃)₂ | 4-X₆-C₆H₄-C(O)NH-C(CH₃)₃ | |
| 333 | X₂—CH(CH₃) | H₃C—X₃ | H | R | (CH₃)₂CHCH₂CH₂—X₅ | 4-X₆-2-methoxy-C₆H₃-C(O)NH-C(CH₃)₃ | |

TABLE 1-continued

| Ex. | R² | R³ | R⁴ | config. R³ or R⁴ | R⁵ | R⁶ | mp. [° C.] |
|---|---|---|---|---|---|---|---|
| 334 | CH₃–X₂ | X₃—CH₃ | X₄—CH₃ | | (CH₃)₂CHCH₂CH₂–X₅ | 4-(N-methylcarbamoyl)-3-methoxyphenyl–X₆ | 250 |
| 335 | CH₃–X₂ | X₃—CH₃ | X₄—CH₃ | | (CH₃)₂CHCH₂CH₂–X₅ | 4-(N-cyclopropylcarbamoyl)phenyl–X₆ | 236 |

In the preceding Table the abbreviations X1 to X6 in the groups specified denote the bond which links the particular group to the corresponding group R1 to R6.

As has been found, the compounds of general formula (I) are characterised by their wide range of applications in the therapeutic field. Particular mention should be made of those applications in which the inhibition of specific cell cycle kinases, particularly the inhibiting effect on the proliferation of cultivated human tumour cells but also the proliferation of other cells, such as endothelial cells, for example, plays a part.

As could be demonstrated by FACS analysis, the inhibition of proliferation brought about by the compounds according to the invention is mediated by the arrest of the cells, particularly at the G2/M phase of the cell cycle. The cells arrest, independently of the cells used, for a specific length of time in this phase of the cell cycle before programmed cell death is initiated. An arrest in the G2/M phase of the cell cycle is triggered, for example, by the inhibition of specific cell cycle kinases. Studies in model organisms such as *Schizosaccharomyces pombe* or Xenopus, or investigations in human cells have shown that the transition from the G2 phase to mitosis is regulated by the CDK1/cyclin B kinase (Nurse, 1990). This kinase, which is also known as the "mitosis promoting factor" (MPF), phosphorylates and thereby regulates a number of proteins, such as e.g. nuclear lamins, kinesin-like motor proteins, condensins and Golgi matrix proteins, which play an important part in the breakdown of the nuclear envelope, in centrosome separation, the formation of the mitotic spindle apparatus, chromosome condensation and the breakdown of the Golgi apparatus (Nigg. E., 2001). A murine cell line with a temperature-sensitive CDK1 kinase mutant shows a rapid breakdown of the CDK1 kinase and a subsequent arrest in the G2/M phase after a temperature increase (Th'ng et al., 1990). The treatment of human tumour cells with inhibitors against CDK1/cyclin B such as e.g. butyrolactone also leads to an arrest in the G2/M phase and subsequent apoptosis (Nishio, et al. 1996). Another kinase which is involved in the G2 and mitosis phase is polo-like kinase 1 (Plk1), which is responsible for the maturation of the centrosomes, for the activation of the phosphatase Cdc25C, as well as for the activation of the anaphase promoting complex (Glover et al., 1998, Qian, et al., 2001). The injection of Plk1 antibodies leads to a G2 arrest in untransformed cells whereas tumour cells arrest in the mitosis phase (Lane and Nigg, 1996). In addition, the protein kinase aurora B has been described as having an essential function during entry into mitosis. Aurora B phosphorylates histone H3 at Ser11 and thereby initiates chromosome condensation (Hsu, J. Y. et al., 2000). A specific cell cycle arrest in the G2/M phase may, however, also be triggered e.g. by the inhibition of specific phosphatases such as e.g. Cdc25C (Russell and Nurse, 1986). Yeasts with a defective cdc25 gene arrest in the G2 phase, while overexpression of cdc25 leads to early entry into the mitosis phase (Russell and Nurse, 1987). However, an arrest in the G2/M phase can also be triggered by the inhibition of certain motor proteins, so-capped kinesins such as e.g. Eg5 (Mayer et al., 1999), or by agents which stabilise or destabilise microtubules (e.g. colchicin, taxol, etoposide, vinblastin, vincristin) (Schiff and Horwitz, 1980).

In view of their biological properties the compounds of general formula I according to the invention, their isomers and their physiologically acceptable salts are suitable for the treatment of diseases characterised by excessive or abnormal cell proliferation.

Such diseases include, for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphoma and solid tumours; skin diseases (e.g. psoriasis); bone diseases; cardiovascular diseases (e.g. restenosis and hypertrophy). They are also suitable for protecting proliferating cells (e.g. hair, intestinal, blood and progenitor cells) from damage to their DNA caused by radiation, UV treatment and/or cytostatic treatment (Davis et al., 2001).

The new compounds may be used for the prevention, short-term or long-term treatment of the abovementioned diseases, also in combination with other active substances used for the same indications, e.g. cytostatics.

The activity of the compounds according to the invention was determined in the cytotoxicity test on cultivated human tumour cells and/or in a FACS analysis, for example on HeLaS3 cells. In both test methods, the compounds exhibited a good to very good activity, i.e. for example an $EC_{50}$ value in the HeLaS3 cytotoxicity test of less than 5 mol, generally less than 1 mol.

Measurement of Cytotoxicity on Cultivated Human Tumour Cells

To measure the cytotoxicity on cultivated human tumour cells, cells of the cervical cancer tumour cell line HeLaS3 (obtained from American Type Culture Collection (ATCC)) in Ham's F12 Medium (Life Technologies) and 10% foetal calf serum (Life Technologies) were cultivated and harvested in the logarithmic growth phase. Then the HeLaS3 cells were placed in 96-well plates (Costar) at a density of 1000 cells per well and incubated overnight in an incubator (at 37° C. and 5% $CO_2$), while on each plate 6 wells were filled only with medium (3 wells as a control of the medium, 3 wells for incubation with reduced AlamarBlue). The active substances were added to the cells in various concentrations (dissolved in DMSO; final concentration: 1%) (in each case as a triple measurement). After 72 hours' incubation, 20 $\mu$l of AlamarBlue (AccuMed International) were added to each well, and the cells were incubated for a further 7 hours. As a control, 20 $\mu$l of reduced Alamar Blue (AlamarBlue reagent which had been autoclaved for 30 min) were added to 3 wells. After 7 h incubation the colour change of the AlamarBlue reagent in the individual wells was determined in a Perkin Elmer fluorescence spectrophotometer (excitation 530 nm, emission 590 nm, slits 15, integrate time 0.1). The amount of AlamarBlue reagent reacted represents the metabolic activity of the cells. The relative cell activity was calculated as a percentage of the control (HeLa S3 cells without inhibitor) and the active substance concentration which inhibits the cell activity by 50% ($IC^{50}$) was obtained. The values were calculated from the average of three individual measurements, correcting for the control value (medium control).

FACS Analysis

Propidium iodide (PI) binds stoichiometrically to double-stranded DNA, and is thus suitable for determining the percentage of cells in the G1, S and G2/M phase of the cell cycle on the basis of the cell DNA content. Cells in the G0 and G1 phase have a diploid DNA content (2N), whereas cells in G2 or mitosis have a 4N DNA content. For PI staining, 0.4 million HeLaS3 cells were seeded, for example, on a 75 $cm^2$ cell culture flask, and after 24 h either 1% DMSO was added as control or the substance was added in various concentrations (in 1% DMSO). The cells were incubated for 24 h with the substance or with DMSO, before the cells were washed with 2×PBS and detached with trypsin/EDTA. The cells were centrifuged (1000 rpm, 5 min, 4° C.), and the cell pellet was washed 2× with PBS, before the cells were resuspended in 0.1 ml of PBS. Then the cells were fixed with 80% ethanol for 16 hours at 4° C. or alternatively for 2 hours at −20° C. The fixed cells ($10^6$ cells) were centrifuged (1000 rpm, 5 min, 4° C.), washed with PBS and then centrifuged again. The cell pellet was resuspended in 2 ml of Triton X-100 in 0.25% PBS, and incubated for 5 min on ice, before 5 ml of PBS were added and the mixture was centrifuged again. The cell pellet was resuspended in 350 $\mu$l of PI stain solution (0.1 mg/ml of Raze A, 10 $\mu$g/ml of presidium iodide in 1×PBS). The cells were incubated for 20 min in the dark with the stain buffer before being transferred into sample measuring vessels for the FACS scan. The DNA measurement was carried out in a Becton Dickinson FACS Analyzer, with an argon laser (500 mW, emission 488 nm), and the DNA Cell Quest Program (BD). The logarithmic PI fluorescence was determined with a band-pass filter (BP 585/42). The cell populations in the individual phases of the cell cycle were quantified with the ModFit LT program of Becton Dickinson.

The compounds of general formula (I) may be used on their own or combined with other active substances according to the invention, optionally also in conjunction with other pharmacologically active substances. Suitable preparations include for example tablets, capsules, suppositories, solutions, particularly solutions for injection (s.c., i.v., i.m.) and infusion, syrups, emulsions or dispersible powders. The amount of pharmaceutically active compound in each case should be in the range from 0.1–90 wt. %, preferably 0.5–50 wt. % of the total composition, i.e. in amounts which are sufficient to achieve the dosage range given below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharin, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as phydroxybenzoates.

Solutions for injection and infusion are prepared in the usual way, e.g. with the addition of preservatives such as p-hydroxybenzoates, or stabilisers such as alkali metal salts of ethylenediamine tetraacefic acid, optionally using emulsifiers and/or dispersants, while if water is used as the diluent organic solvents may optionally be used as solubilisers or auxiliary solvents, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Suitable excipients may be, for example, water, pharmaceutically acceptable organic solvents, such as paraffins (e.g. petroleum fractions), oils of vegetable origin (e.g. groundnut or sesame oil), mono- or polyfunctional alcohols (e.g. ethanol or glycerol), carriers such as e.g. natural mineral powders (e.g. kaolin, clays, talc, chalk), synthetic mineral powders (e.g. highly dispersed silica and silicates), sugar (e.g. glucose, lactose and dextrose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered in the usual way, preferably by oral or transdermal route, particularly preferably by oral route. When administered orally the tablets may, of course, contain additives, such as e.g. sodium citrate, calcium carbonate and dicalcium phosphate together with various additives, such as starch, preferably potato starch, gelatine and the like, in addition to the abovementioned carriers. Lubricants such as magnesium stearate, sodium laurylsulphate and talc may also be used to form tablets. In the case of aqueous suspensions the active substances may be combined with various flavour enhancers or colourings in addition to the abovementioned excipients.

For parenteral use, solutions of the active substances may be prepared using suitable liquid carrier materials.

The dosage for intravenous use is 1–1000 mg per hour, preferably between 5–500 mg per hour.

However, it may optionally be necessary to deviate from the amounts specified, depending on the body weight or method of administration, the individual response to the medication, the nature of the formulation used and the time or interval over which it is administered. Thus, in some cases, it may be sufficient to use less than the minimum quantity specified above, while in other cases the upper limit specified will have to be exceeded. When large amounts are administered it may be advisable to spread them over the day in a number of single doses.

The formulation examples that follow illustrate the present invention without restricting its scope:

Examples of Pharmaceutical Formulations

| A) | Tablets | per tablet |
|---|---|---|
| | active substance | 100 mg |
| | lactose | 140 mg |
| | corn starch | 240 mg |

-continued

| A) | Tablets | per tablet |
|---|---|---|
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | lactose | 55 mg |
| | corn starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

What is claimed is:

1. A compound of the formula (I),

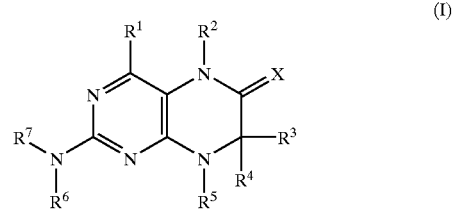

wherein
$R^1$ denotes a group selected from among hydrogen, $NH_2$, XH, halogen and a $C_1$–$C_3$-alkyl group optionally substituted by one or more halogen atoms, $R^2$ denotes a group selected from among hydrogen, CHO, XH, —X—$C_1$–$C_2$-alkyl and an optionally substituted $C_1$–$C_3$-alkyl group, $R^3$, $R^4$ are identical or different and denote a group selected from among optionally substituted $C_1$–$C_{10}$-alkyl, $C_2$–$C_{10}$-alkenyl, $C_2$–$C_{10}$-alkynyl, aryl, heteroaryl, $C_3$–$C_8$-cycloalkyl, $C_3$–$C_8$-heterocycloalkyl, —X—aryl, —X—heteroaryl, —X—cycloalkyl, —X—heterocycloalkyl, —$NR^8$-aryl, —$NR^8$-heteroaryl, —$NR^8$-cycloalkyl, and —$NR^8$-heterocycloalkyl, or a group selected from among hydrogen, halogen, $COXR^8$, $CON(R^8)_2$, $COR^8$ and $XR^8$, or $R^3$ and $R^4$ together denote a 2- to 5-membered alkyl bridge which may contain 1 to 2 heteroatoms, $R^5$ denotes hydrogen or a group selected from among optionally substituted $C_1$–$C_{10}$-alkyl, $C_2C_{10}$-alkenyl, $C_2$–$C_{10}$-alkynyl, aryl, heteroaryl and —$C_3$–$C_6$-cycloalkyl, or $R^3$ and $R^5$ or $R^4$ and $R^5$ together denote a saturated or unsaturated $C_3$–$C_4$-alkyl bridge which may contain 1 to 2 heteroatoms, $R^6$ denotes optionally substituted aryl or heteroaryl, $R^7$ denotes hydrogen or —CO—X—$C_1$–$C_4$-alkyl, and X in each case independently of one another denotes O or S, and $R^8$ in each case independently of one another denotes hydrogen or a group selected from among optionally substituted $C_1$–$C_4$-alkyl, $C_2$–$C_4$-alkenyl, $C_2$–$C_4$-alkynyl and phenyl, or the tautomers, the racemates, the enantiomers, the diastereomers and the mixtures thereof, and optionally the pharmacologically acceptable acid addition salts thereof.

2. The compound according to claim 1, wherein $R^1$ denotes hydrogen, $R^2$ denotes a group selected from among a CHO, OH, and $CH_3$ group, $R^3$, $R^4$ are identical or different and denote a group selected from among hydrogen, optionally substituted $C_1$–$C_6$-alkyl, $C_2$–$C_6$-alkenyl, $C_2$–$C_6$-alkynyl, $C_3$–$C_7$-cycloalkyl, or $R^3$ and $R^4$ together denote a $C_2$–$C_5$-alkyl bridge, $R^5$ denotes a group selected from among optionally substituted $C_1$–$C_{10}$-alkyl, $C_2$–$C_{10}$-alkenyl, $C_2$–$C_{10}$-alkynyl, $C_3$–$C_6$-cycloalkyl and $C_3$–$C_6$-cycloalkenyl, or $R^3$ and $R^5$ or $R^4$ and $R^5$ together denote a saturated or unsaturated $C_3$–$C_4$-alkyl bridge which may contain 1 to 2 heteroatoms, and $R^7$ denotes hydrogen.

3. The compound according to claim 2, wherein $R^1$–$R^5$, $R^7$, $R^8$ and X have the meaning indicated, and $R^6$ denotes a group of general formula

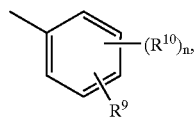

wherein n denotes 1, 2, 3 or 4, $R^9$ denotes a group selected from among optionally substituted $C_1$–$C_6$-alkyl, $C_2$–$C_6$-alkenyl, $C_2$–$C_6$-alkynyl, —CONH—$C_1$–$C_{10}$-alkylene, —O-aryl, —O-heteroaryl, —O-cydoalkyl, —O-heterocycloalkyl, aryl, heteroaryl, cycloalkyl and heterocycloalkyl or a group selected from among —O—$C_1$–$C_6$-alkyl-$Q^1$, —$CONR^8$—$C_1$–$C_{10}$-alkyl-$Q^1$, —$CONR^8$—$C_2$–$C_{10}$-alkenyl-$Q^1$, —$CONR^8$—$Q^2$, halogen, OH, —$SO_2R^8$, —$SO_2N(R^8)_2$, —$COR^8$, —$COOR^8$, —$N(R^8)_2$, —$NHCOR^8$, $CONR^8OC_1$–$C_{10}$ alkyl$Q^1$ and $CONR^8OQ^2$, $Q^1$ denotes hydrogen, —$NHCOR^8$, or a group selected from among an optionally substituted —NH-aryl, —NH-heteroaryl, aryl, heteroaryl, $C_3$–$C_8$-cycloalkyl- and heterocycloalkyl group, $Q^2$ denotes hydrogen or a group selected from among an optionally substituted aryl, heteroaryl, $C_3$–$C_8$-heterocycloalkyl, $C_3$–$C_8$-cycloalkyl- and $C_1$–$C_4$-alkyl-$C_3$–$C_8$-cycloalkyl group, $R^{10}$ is identical or different and denotes a group selected from among optionally substituted $C_1$–$C_6$-alkyl, $C_2$–$C_6$-alkenyl and $C_2$–$C_6$-alkynyl, —O—$C_1$–$C_6$-alkyl, —O—$C_2$–$C_6$-alkenyl, —O—$C_2$–$C_6$-alkynyl, $C_3$–$C_6$heterocycloalkyl and $C_3$–$C_3$–$C_6$-cycloalkyl, or a group selected from among hydrogen, —$CONH_2$, —$COOR^8$, —$OCON(R^8)_2$, —$N(R^8)_2$, —$NHCOR^8$, —$NHCON(R^8)_2$, —$NO_2$ and halogen, or adjacent groups $R^9$ and $R^{10}$ together denote a bridge of the formula

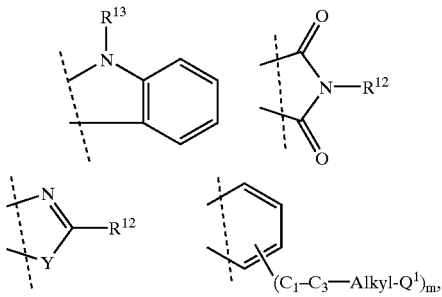

Y denotes O, S or $NR^{11}$, m denotes 0, 1 or 2

$R^{11}$ denotes hydrogen or $C_1$–$C_2$-alkyl, and $R^{12}$ denotes hydrogen or a group selected from among optionally substituted phenyl, pyridyl, pyrazinyl, pyrimidinyl, pyridazinyl, —$C_1$–$C_3$-alkyl-phenyl, —$C_1$–$C_3$-alkyl-pyridyl, —$C_1$–$C_3$-alkyl-pyrazinyl, —$C_1$–$C_3$-alkyl-pyrimidinyl and —$C_1$–$C_3$-alkyl-pyridazinyl, and $R^{13}$ denotes $C_1$–$C_6$-alkyl.

4. The compounds according to claim 3, wherein $R^1$ denotes hydrogen, $R^2$ denotes $CH_3$, and $R^7$ denotes hydrogen.

5. A pharmaceutical composition comprising a pharmaceutically effective amount of a compound of formula I according to claim 1 optionally combined with conventional excipients and/or carriers.

6. A method of inhibiting proliferation of cells in a patient in need thereof, said method comprising administering to a patient in need thereof a therapeutically effective amount of a compound of formula I according to claim 1.

7. The method according to claim 6 wherein the cells are tumour cells, endothelial, hair, intestinal, blood or progenitor cells.

8. A process for preparing a compound of the formula (I) according to claim 1,

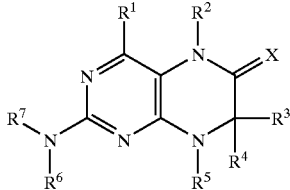
(I)

wherein $R^1$–$R^7$ and X are as defined in claim 1, comprising reacting a compound of the formula (II)

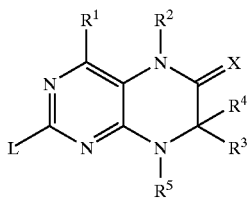
(II)

wherein

L is a leaving group, with an optionally substituted compound of the formula (III)

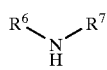
(III)

wherein $R^6$ and $R^7$ are as defined in claim 1, and subsequently isolating the product compound.

9. A compound of the formula (II),

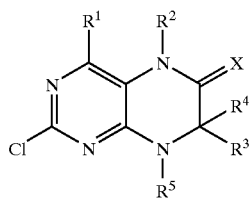
(II)

wherein $R^1$–$R^5$ and X have the meanings given in claims 1 to 4.

10. A process for preparing a compound of the formula (I),

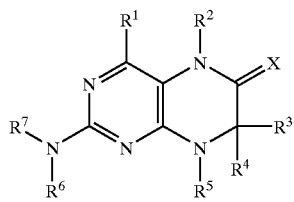
(I)

wherein $R^6$ denotes a group of the formula:

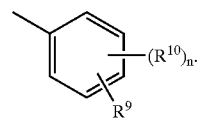

$R^9$ denotes an optionally substituted group —CONH— $C_1$–$C_{10}$-alkylene or a group selected from among —CONR$^8$—$C_1$–$C_{10}$-alkyl-$Q^1$, —CONR$^8$—$C_2$–$C_{10}$-alkenyl-$Q^1$, —CONR$^8$—$Q^2$, and —COOR$^8$, and $R^1$–$R^5$, $R^7$, $R^{10}$, n and X are as defined as in claim 1, comprising reacting a compound of the formula (IA),

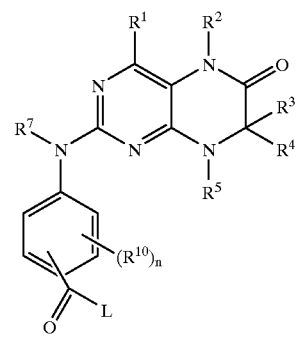
(IA)

wherein $R^1$ to $R^5$, $R^7$, $R^{10}$ and n are as defined as in claim 1, and L denotes a leaving group with a primary or secondary amine to form the corresponding amide; or reaching a compound of the formula (IA) with an alcohol to form the corresponding ester;

and subsequently isolating the product compound.

* * * * *